United States Patent
Okada et al.

(10) Patent No.: US 10,172,695 B2
(45) Date of Patent: Jan. 8, 2019

(54) METHOD FOR MANUFACTURING DENTAL MILL BLANK

(71) Applicant: KURARAY NORITAKE DENTAL INC., Kurashiki-shi (JP)

(72) Inventors: Koichi Okada, Chiyoda-ku (JP); Takehiro Kameya, Tainai (JP); Hiroshige Ishino, Tainai (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 68 days.

(21) Appl. No.: 14/416,351

(22) PCT Filed: Jul. 30, 2013

(86) PCT No.: PCT/JP2013/070650
§ 371 (c)(1),
(2) Date: Jan. 22, 2015

(87) PCT Pub. No.: WO2014/021343
PCT Pub. Date: Feb. 6, 2014

(65) Prior Publication Data
US 2015/0182315 A1 Jul. 2, 2015

(30) Foreign Application Priority Data

Jul. 31, 2012 (JP) ................. 2012-170294

(51) Int. Cl.
| A61C 8/00 | (2006.01) |
| A61C 13/00 | (2006.01) |
| A61C 13/087 | (2006.01) |
| A61C 13/08 | (2006.01) |

(52) U.S. Cl.
CPC ...... *A61C 13/0006* (2013.01); *A61C 13/0004* (2013.01); *A61C 13/0022* (2013.01); *A61C 13/082* (2013.01); *A61C 13/087* (2013.01)

(58) Field of Classification Search
CPC . A61C 13/006; A61C 13/0022; A61C 13/082; A61C 13/087; A61C 13/0004; A61K 6/083; A61K 8/1816; C04B 35/488
See application file for complete search history.

(56) References Cited

U.S. PATENT DOCUMENTS

| 3,990,149 | A | 11/1976 | Nedwig |
| 5,869,548 | A | 2/1999 | Ikushima et al. |
| 5,990,195 | A | 11/1999 | Arita |
| 6,159,417 | A | 12/2000 | Giordano |
| 6,186,790 | B1 * | 2/2001 | Karmaker ............... A61C 5/007 433/180 |
| 6,379,593 | B1 * | 4/2002 | Datzmann .......... A61C 13/0022 264/16 |
| 6,599,125 | B1 * | 7/2003 | Freilich .................. A61C 5/007 433/180 |
| 7,255,562 | B2 | 8/2007 | Rusin et al. |
| 7,845,947 | B2 | 12/2010 | Rusin et al. |
| 8,317,516 | B2 | 11/2012 | Rusin et al. |
| 2001/0036617 | A1 * | 11/2001 | Karmaker ............... A61C 5/007 433/173 |
| 2003/0157357 | A1 | 8/2003 | Rusin et al. |
| 2004/0241614 | A1 * | 12/2004 | Goldberg ........... A61C 13/0003 433/202.1 |
| 2005/0031704 | A1 | 2/2005 | Ahn |
| 2005/0164045 | A1 | 7/2005 | Rothbrust et al. |
| 2008/0118894 | A1 | 5/2008 | Rothbrust et al. |
| 2010/0003630 | A1 * | 1/2010 | Yamashita ............. B82Y 30/00 433/8 |
| 2011/0027742 | A1 * | 2/2011 | Fujisaki ................ C04B 35/486 433/8 |
| 2011/0046260 | A1 | 2/2011 | Okubayashi et al. |
| 2011/0104643 | A1 * | 5/2011 | Giordano ........... A61C 13/0022 433/203.1 |
| 2011/0183297 | A1 | 7/2011 | Thiel et al. |
| 2011/0229858 | A1 | 9/2011 | Sadoun |
| 2011/0318402 | A1 | 12/2011 | Ahn |
| 2012/0022648 | A1 | 1/2012 | Vult Von Steyern |
| 2012/0064490 | A1 | 3/2012 | Rothbrust et al. |
| 2013/0172441 | A1 * | 7/2013 | Takahata ............ A61C 13/0022 523/115 |
| 2014/0056950 | A1 | 2/2014 | Ahn |
| 2014/0227654 | A1 * | 8/2014 | Fujisaki ................ C04B 35/486 433/8 |
| 2015/0093721 | A1 * | 4/2015 | Nakamura .......... A61C 13/0022 433/206 |
| 2015/0182315 | A1 * | 7/2015 | Okada .................. A61C 13/087 433/202.1 |
| 2015/0216636 | A1 * | 8/2015 | Nakamura .......... A61C 13/0004 433/207 |
| 2015/0315086 | A1 * | 11/2015 | Kawamura .......... A61K 6/0005 501/134 |

FOREIGN PATENT DOCUMENTS

| CN | 102098979 A | 6/2011 |
| CN | 102149348 A | 8/2011 |
| CN | 102341060 A | 2/2012 |
| EP | 0 803 241 A2 | 10/1997 |
| EP | 0 803 241 A3 | 10/1997 |
| JP | 2-84952 A | 3/1990 |
| JP | 2-85205 A | 3/1990 |
| JP | 10-323353 A | 12/1998 |
| JP | 2000-185058 A | 7/2000 |

(Continued)

OTHER PUBLICATIONS

International Search Report dated Sep. 3, 2013 in PCT/JP2013/070650.

(Continued)

*Primary Examiner* — Nicholas Lucchesi
(74) *Attorney, Agent, or Firm* — Oblon, McClelland, Maier & Neustadt, L.L.P.

(57) ABSTRACT

A method for producing a dental mill blank, characterized in that the method includes contacting an inorganic filler molded article produced by subjecting an inorganic filler to press molding and a polymerizable monomer-containing composition, and allowing the polymerizable monomer to polymerize and cure. When the method of the present invention is used, a dental mill blank having a high inorganic powder content and excellent mechanical strength is obtained. In addition, the dental mill blank obtained is suitably used in the fabrication of a dental prosthesis having high mechanical strength and excellent gloss retention, by machining a mill blank using a CAD/CAM system.

24 Claims, No Drawings

(56) References Cited

FOREIGN PATENT DOCUMENTS

| JP | 2001-279106 A | 10/2001 |
| JP | 2003-529386 A | 10/2003 |
| JP | 2004-324091 A | 11/2004 |
| JP | 2011-528597 A | 11/2011 |
| JP | 2012/501783 A | 1/2012 |
| JP | 2012-87204 A | 5/2012 |
| WO | WO 2009/133913 A1 | 11/2009 |
| WO | WO 2009/154301 A1 | 12/2009 |
| WO | WO 2010/101523 A1 | 9/2010 |
| WO | WO 2012/042911 A1 | 4/2012 |

OTHER PUBLICATIONS

Li-Hong He, et al., "A novel polymer infiltrated ceramic dental material", Dental Materials, vol. 27, (2011), pp. 527-534.
Combined Office Action and Search Report dated Sep. 1, 2015 in Chinese Patent Application No. 201380040851.2 (with English Translation of Category of Cited Documents).
Extended European Search Report dated Feb. 19, 2016 in Patent Application No. 13826054.2.

* cited by examiner

METHOD FOR MANUFACTURING DENTAL MILL BLANK

This application is a National Stage of PCT/JP2013/070650, which was filed on Jul. 30, 2013. This application is based upon and claims the benefit of priority to Japanese Application No. 2012-170294, which was filed on Jul. 31, 2012.

TECHNICAL FIELD

The present invention relates to a method for producing a dental mill blank, and a dental mill blank obtained by the method. More specifically, the present invention relates to a method for producing a dental mill blank usable in, for example, fabrications of dental prostheses such as inlay, onlay, onlay, veneer, crown, bridge, abutment tooth, dental post, denture, denture base, implant members (fixtures and abutments), by machining with a dental CAD/CAM system.

BACKGROUND ART

In recent years, CAD/CAM systems have been widely used to design dental prostheses such as inlays and crowns by computers to fabricate them by machining with milling machines. Conventionally, because of the importance laid on the aesthetic properties, ceramic materials have been generally used as the materials for mill blanks, which are materials to be machined usable in the present systems. However, since dental prostheses fabricated from mill blanks made of ceramics are brittle materials having high hardness, there are some disadvantages such as damages to opposing teeth or tooth chips caused by impact upon machining, occlusion, etc.

In order to solve the above problems, recently, studies on mill blanks made of composite materials containing a polymer resin or an inorganic filler have been made. Since the mill blanks made of the composite material have appropriate hardness that does not damage opposing teeth, and excellent impact resistance, the mill blanks have been worked into dental prostheses and be begun using them in clinical practices.

For example, Patent Publication 1 describes a mill blank for fabricating a dental prosthesis containing a polymer resin and an inorganic filler. As the fillers, a filler prepared by finely pulverizing a material obtained by sol-gel method, a commercially available irregular shaped barium glass filler, a filler prepared by pulverizing quartz with a mill, and an ultrafine particle inorganic filler (average particle size: 40 nm) have been studied.

In addition, Patent Publication 2 describes a mill blank for fabricating a dental prosthesis, containing an acrylic resin polymer and an ultrafine particle inorganic filler having an average particle size of from 0.01 to 0.04 μm.

Patent Publication 3 describes a resin cured product for dental medical care, comprising inorganic particles (composite particles) having a coating phase constituted by an acrylic polymer containing fluorine, and an acrylic polymer.

Patent Publication 4 describes a dental mill blank comprising a cured product of a curable composition containing a polymerizable monomer and a spherical inorganic filler having an average primary particle size of 0.1 μm or more and less than 1 μm.

Patent Publication 5 describes a method for producing a block for dental prosthesis process, including the steps of preparing a template provided with an inner surface shape corresponding to an outer surface shape of the block, filling a composite resin material containing a resin and an inorganic filler dispersed therein, capable of forming the above block by a curing treatment, subjecting the above composite resin to a rotary stirring treatment, while housing the above composite resin in the above template, and polymerizing the above composite resin material after the stirring treatment to cure. More specifically, it is a method for producing a block for dental prosthesis process, including filling a composite resin material containing an inorganic filler to a template having a block shape, rotary-stirring the contents to allow degassing, and thereafter allowing the composite resin material to polymerize and cure.

Patent Publication 6 describes a composite material suitable for a dental mill blank having a cross-network structure of glass and an organic resin, obtained by immersing a monomer in a porous support obtained by fritting glass powder, and thereafter allowing the monomer to polymerize and cure.

Further, Non-Patent Publication 1 describes a composite material suitable in dental mill blank obtained by immersing a polymer resin, or immersing a monomer and thereafter allowing the monomer to polymerize and cure, in a porous bulk-shaped ceramic sintered body having a communicated structure, thereby providing a dental mill blank having a interpenetrating network structure of ceramics and organic resins.

PRIOR ART REFERENCES

Patent Publications

Patent Publication 1: Japanese Unexamined Patent Publication No. 2003-529386
Patent Publication 2: Japanese Patent Laid-Open No. Hei-10-323353
Patent Publication 3: Japanese Patent Laid-Open No. 2012-87204
Patent Publication 4: WO 2012/042911
Patent Publication 5: WO 2009/154301
Patent Publication 6: Japanese Unexamined Patent Publication No. 2012-501783

Non-Patent Publications

Non-Patent Publication 1: Dental Materials 27(2011), 527-534

SUMMARY OF THE INVENTION

Problems to be Solved by the Invention

However, in any one of the above Patent Publications 1 to 5, a homogeneous paste-like composition (composite resin) obtained by mixing and kneading an inorganic filler and a polymerizable monomer is injected into a template, and the composition is subjected to thermal polymerization or photopolymerization in the template, thereby giving a cured product, which is referred to as a mill blank. In a method of obtaining a mill blank including preparing first a composite resin, and allowing the composite resin to polymerize and cure as described above, the composite resin before the polymerization needs to have a certain degree of high flowability, thereby making it difficult to increase a blending ratio of the inorganic filler. As a result, in a dental prosthesis obtained from the mill blank, sufficient mechanical strength cannot be obtained, and abrasion resistance and surface gloss are also not sufficient. Further, the step of producing a composite resin including mixing an inorganic filler and a polymerizable monomer is necessary, so that a production cost would be higher accordingly.

In addition, a dental mill blank described in Patent Publication 6 has a structure in which a resin is immersed in a bulk-shaped glass porous member, and pores not being communicated upon fitting may be formed, thereby causing undesired disadvantages that a part in which the resin is not immersed is produced, or that normal opposing teeth is abraded due to the ruggedness of glass having high hardness. A dental mill blank described in Non-Patent Publication 1 has a structure in which a resin is immersed in a bulk-shaped ceramic porous member, so that it is basically nothing more than a brittle material similar to ceramics.

The present invention is accomplished in order to solve the above problems held by the prior art, and an object thereof is to provide a convenient method for producing a dental mill blank capable of providing a dental prosthesis having excellent mechanical strength, having excellent abrasion resistance and surface gloss, and giving excellent abrasion resistance of opposing teeth.

Means to Solve the Problems

The present invention relates to the followings [1] to [6]:
[1] a method for producing a dental mill blank, characterized in that the method includes contacting an inorganic filler molded article produced by subjecting an inorganic filler to press molding and a polymerizable monomer-containing composition, and allowing the polymerizable monomer to polymerize and cure;
[2] a dental mill blank obtained by a method as defined in the above [1];
[3] a dental prosthesis fabricated by machining from a dental mill blank as defined in the above [2];
[4] a dental mill blank obtained by a method as defined in the above [1], wherein ultrafine inorganic particles having an average particle size of from 0.001 to 0.1 µm are contained in an amount of from 65 to 95% by weight of the mill blank;
[5] a dental mill blank obtained by a method as defined in the above [1], wherein inorganic particles having an average particle size of from 0.1 to 1 µm are contained in an amount of from 80 to 95% by weight of the mill blank; and
[6] a dental mill blank obtained by a method as defined in the above [1], wherein ultrafine inorganic particles having an average particle size of from 0.001 to 0.1 µm and inorganic particles having an average particle size of from 0.2 to 2 µm are contained in a total amount of from 80 to 96% by weight of the mill blank.

Effects of the Invention

The dental mill blank obtained by the method for producing a dental mill blank of the present invention has high mechanical properties and excellent abrasion resistance and gloss retention by machining the dental mill blank using a CAD/CAM system, and is capable of providing a dental prosthesis with aesthetic properties also having excellent abrasion resistance of opposing teeth. Here, in the present invention, the term "dental mill blank" refers to a solid block of a material from which a dental prosthesis can be fabricated by cutting, carving or milling.

MODES FOR CARRYING OUT THE INVENTION

The method for producing a dental mill blank of the present invention is characterized in that the method includes contacting an inorganic filler molded article produced by subjecting an inorganic filler (also called an inorganic filler) to press molding and a polymerizable monomer-containing composition, and allowing the polymerizable monomer to polymerize and cure. More specifically, in the method for producing a dental mill blank of the present invention, an inorganic filler is subjected to press molding, to prepare a molded article having a bulk shape of an appropriate size in which an inorganic filler is aggregated. The molded article has a structure in which individual inorganic fillers are filled in close contact, not a porous structure as obtained by sintering an inorganic filler. Next, a polymerizable monomer is allowed to contact with the molded article, thereby allowing the polymerizable monomer to infiltrate into interstitials of primary particles of the inorganic filler constituting the molded article, and the polymerizable monomer is allowed to polymerize and cure in that state, thereby making it possible to obtain a dental mill blank in which the inorganic filler is filled very densely. In this point, the method is completely different from a method for producing a dental mill blank, as conventionally known, including homogeneously mixing and kneading an inorganic filler and a polymerizable monomer to give a paste-like polymerizable composition (composite resin) having flowability, and subsequently allowing the polymerizable composition (composite resin) to polymerize and cure. Furthermore, in the dental mill blank obtained by the present invention, a cured product having an inorganic filler content far exceeding than that accomplished in the conventional dental composite resin can be provided.

As the inorganic filler usable in the present invention, known inorganic particles which are usable as fillers for dental composite resins are used without any limitations. Specifically, for example, conventionally known materials, including various kinds of glass {containing silicon dioxide (silica, quartz, silica gel etc.), or silicon as a main component, and containing boron and/or aluminum together with various heavy metals}, alumina, various ceramics, diatomaceous earth, kaolin, clay minerals (montmorillonite etc.), activated white clay, synthetic zeolite, mica, silica, calcium fluoride, ytterbium fluoride, calcium phosphate, barium sulfate, zirconium dioxide (zirconia), titanium dioxide (titania), or hydroxyapatite, etc. can be used. Also, there are no problems in using organic-inorganic composite particles (organic-inorganic composite filler) obtainable by previously adding a polymerizable monomer to these inorganic particles to give a paste-like form, thereafter allowing the polymerizable monomer to polymerize and cure, and pulverizing a cured product. These inorganic particles may be used alone or in combination of two or more kinds.

In addition, important physical properties desirable for dental crown restorative materials include transparency and radiopacity, in the same manner as in natural teeth. The transparency is accomplished by making a refractive index of the inorganic filler in agreement with that of the polymerizable monomer after curing as much as possible. In addition, in order to give radiopacity, an inorganic oxide containing a heavy metal element, such as zirconium, barium, titanium, lanthanum, or strontium is used. The refractive index of an inorganic filler containing a heavy metal element as mentioned above is usually high, within the range of from 1.5 to 1.6. Accordingly, in the present invention, for example, in a case where a (meth)acrylate-based monomer is used as a polymerizable monomer, since the refractive index of the (meth)acrylate-based monomer is usually within the range of (from 1.5 to 1.6, the difference in refractive indexes can be regulated to be small even when used in combination with inorganic particles having a high refractive index which has radiopacity as mentioned above. Therefore, the dental mill blank obtained is likely to have high transparency and is useful.

The inorganic particles having high refractive indexes which have radiopacity include, for example, barium boroaluminosilicate glass (e.g., E3000 manufactured by Esstech, Inc.; 8235, GM27884, GM39923 manufactured by SCHOTT), strontium boroaluminosilicate glass (e.g., E4000 manufactured by Esstech, Inc.; G018-093, GM32087 manufactured by SCHOTT), lanthanum glass (e.g., GM31684 manufactured by SCHOTT), fluoroaluminosilicate glass (e.g., G018-091, G018-117 manufactured by SCHOTT), zirconia-containing glass (e.g., G018-310, G018-159 manufactured by SCHOTT), strontium-containing glass (e.g., G018-163, G018-093, GM32087 manufactured by SCHOTT), zinc oxide-containing glass (e.g., G018-161 manufactured by SCHOTT), calcium-containing glass (e.g., G018-309 manufactured by SCHOTT), etc.

The inorganic particles usable as an inorganic filler in the present invention is not particularly limited in the shapes, and the inorganic particles in, for example, various shapes, such as disrupted shape, plate-like shape, scale-like shape, fibrous shape (short fiber, long fiber), acicular shape, whisker, and spherical shape are used. The shapes may be an aggregated form of primary particles of these shapes, or may be a combination of different shapes. Here, in the present invention, the inorganic particles may be those that are subjected to some sort of treatments (e.g. pulverization) so as to have the shapes mentioned above.

In addition, the particle sizes of these inorganic particles may be sizes to an extent that is ordinarily usable as a filler for a dental composite resin, so long as the inorganic particles can be subjected to press molding. For example, the inorganic particles include inorganic particles having an average particle size of from 0.001 to 10 μm and a particle size range of from 0.0005 to 50 μm. Preferably, inorganic particles have an average particle size of from 0.002 to 5 μm and a particle size range of from 0.0005 to 20 μm, more preferably, inorganic particles have an average particle size of from 0.005 to 3 μm and a particle size range of from 0.001 to 10 μm, and even more preferably, inorganic particles have an average particle size of from 0.005 to 1 μm and a particle size range of from 0.001 to 3 μm are used. Here, the particle size of the inorganic particles as used herein means a particle size of primary particles of inorganic particles (average primary particle size), and the particle size range refers to a range of particle sizes satisfied by 95% or more of the particles of the population used, and particles not satisfying the particle size range defined may be contained without particular limitations, within the range that would not impair the effects of the present invention.

Here, the average particle size of the inorganic particles as used herein can be obtained according to a laser diffraction scattering method or an electron microscopic observation of the particles. Specifically, in the particle size measurement of particles having sizes of 0.1 μm or more, the laser diffraction scattering method is conveniently used, and in the particle size measurement of ultrafine particles having sizes of 0.1 μm or less, the electron microscopic observation is conveniently used.

In the laser diffraction scattering method, for example, the measurements can be made with a laser diffraction particle size distribution analyzer (SALD-2100, manufactured by Shimadzu Corporation) using a 0.2% aqueous sodium hexametaphosphate as a dispersion medium.

In the electron microscopic observation, for example, the measurements can be made by taking a photograph of particles with a transmission electron microscope (manufactured by Hitachi Limited, Model H-800NA), and measuring particle sizes of particles (200 or more in number) observed within unit field of view in the photograph with a software for an image analysis-type particle size distribution measurement (Mac-view (Mountech Co., Ltd.)). In this measurement, a particle size of particles is obtained as a projected area diameter, which is a diameter of a circle having an identical area to the particles, and an average primary particle size is calculated from the number of particles and particle sizes thereof.

In the present invention, the above inorganic particles may be molded by subjecting inorganic particles to press molding, to give a molded article made of an inorganic filler, i.e. an inorganic filler molded article. Accordingly, so long as the above-mentioned molded article can be produced, two or more kinds of inorganic particles having different materials, particle size distributions, and shapes may be mixed or used in combination. Also, particles other than the inorganic particles may be contained unintentionally as impurities, within the range that would not impair the effects of the present invention.

Preferred embodiments of the inorganic filler in the present invention include the followings.

In the present invention, in one of preferred embodiments, it is preferable that the inorganic filler contains inorganic particles having an average particle size of from 0.1 to 1 μm and a particle size range of from 0.05 to 5 μm, i.e. a submicron filler. Among them, inorganic particles having the above-mentioned particle size range and having an average particle size of preferably from 0.1 to 0.5 μm, and more preferably from 0.1 to 0.3 μm are preferred. Specifically, inorganic particles having an average particle size within the range of from 0.1 to 1 μm, and a particle size range of from 0.05 to 5 μm are preferred, inorganic particles having an average particle size within the range of from 0.1 to 0.5 μm, and a particle size range of from 0.05 to 5 μm are more preferred, and inorganic particles having an average particle size within the range of from 0.1 to 0.3 μm, and a particle size range of from 0.05 to 5 μm are even more preferred. The application of the inorganic particles having particle sizes within this range can give a dental mill blank that gives a dental prosthesis appropriately having both mechanical strength and aesthetic properties (abrasion resistance and gloss). The content of the submicron filler in a case where the above-mentioned submicron filler is applied is preferably 90% by weight or more, more preferably 95% by weight or more, and even more preferably substantially 100% by weight, of the inorganic filler.

In addition, in the submicron filler having a particle size range as such, a case where the inorganic particles are spherical particles is more preferred, from the viewpoint mentioned above. The spherical particles include nearly spherical particles, and do not necessarily need to be perfectly spherical. In general, when a photograph of particles is taken using a scanning electronic microscope, 30 particles observed in a unit field of view of the photograph are arbitrarily selected, and then an aspect ratio is obtained by dividing particle sizes in a direction orthogonal to a maximum size for each of the particles by its maximum size, an average thereof (average aspect ratio) is preferably 0.6 or more, more preferably 0.8 or more, and even more preferably 0.9 or more.

The spherical submicron filler as mentioned above is preferably silica particles; oxide particles of at least one metal selected from the group consisting of Group 2, Group 4, Group 12, and Group 13 metals of the Periodic Table; or composite oxide particles containing at least one metal atom selected from the group consisting of Group 2, Group 4, Group 12, and Group 13 metals of the Periodic Table, silicon atom, and oxygen atom. Specific examples of these spherical submicron fillers include particles of amorphous silica, quartz, cristobalite, and tridymite; alumina, titanium dioxide, strontium oxide, barium oxide, zinc oxide, zirconium oxide, and hafnium oxide; silica-zirconia, silica-titania, silica-titania-barium oxide, silica-alumina, silica-titania-sodium oxide, silica-titania-potassium oxide, silica-zirconia-sodium oxide, silica-zirconia-potassium oxide, silica-barium oxide, silica-strontium oxide, etc. More preferred spherical particles are silica particles; oxide particles of Group 4 metals of the Periodic Table; or composite oxide particles containing a metal atom of Group 4 metals of the Periodic Table, a silicon atom, and an oxygen atom, and even more preferred spherical particles are silica-zirconia particles, from the viewpoint of obtaining a dental mill blank having radiopacity and more excellent abrasion resistance. The methods for producing spherical inorganic particles are described specifically, for example, in a patent publication Japanese Patent Laid-Open No. Sho-58-110414 or WO 2009/133913. In addition, hydroxyapatite can also be used as a spherical inorganic powder.

Here, the above-mentioned submicron filler has a specific surface area of preferably from 5 to 25 $m^2/g$. The specific surface area as used herein can be measured in accordance with an ordinary method by a specific surface area BET method.

When the spherical submicron filler is used, it is difficult that the content of the inorganic filler in a case of a dental composite resin produced in accordance with an ordinary method substantially exceeds 80% by weight, in accordance with the studies by the present inventors. However, the content of the inorganic filler of 80% by weight or more can be obtained in the dental mill blank of the present invention. When the above-mentioned submicron filler is used, the content of the inorganic filler is within the range of preferably 80% by weight or more, more preferably 81% by weight or more, even more preferably 82% by weight or more, and even more preferably 84% by weight or more, and preferably 95% by weight or less, and more preferably 92% by weight or less, of the dental mill blank in the present invention. In addition, the content is within the range of preferably from 80 to 95% by weight, more preferably from 82 to 92% by weight, and even more preferably from 84 to 92% by weight. Here, the content in the dental mill blank as used herein means a content per unit weight of the dental mill blank.

Also, in one of another preferred embodiments, it is preferable that an inorganic filler contains inorganic particles having an average particle size within the range of from 0.001 to 0.1 μm and a specific surface area within the range of from 500 to 30 $m^2/g$. The above-mentioned inorganic particles as used herein may be described as ultrafine inorganic particles. Specifically, in one of another preferred embodiments of the present invention, it is preferable that an inorganic filler contains ultrafine inorganic particles having an average particle size of from 0.001 to 0.1 μm and a specific surface area within the range of from 500 to 30 $m^2/g$. Among them, it is preferable that ultrafine inorganic particles have an average particle size of within the range of preferably 0.005 μm or more, and more preferably 0.01 μm or more, and preferably 0.05 μm or less, and more preferably 0.04 μm or less, and have a specific surface area of within the range of preferably 40 $m^2/g$ or more, and more preferably 50 $m^2/g$ or more, and preferably 400 $m^2/g$ or less, and more preferably 200 $m^2/g$ or less. In addition, it is preferable that the ultrafine inorganic particles have an average particle size of preferably from 0.005 to 0.05 μm, and more preferably from 0.01 to 0.04 μm, and have a specific surface area of preferably from 400 to 40 $m^2/g$, and more preferably from 200 to 50 $m^2/g$. In other words, ultrafine inorganic particles having an average particle size within the range of from 0.005 to 0.05 μm, and having a specific surface area within the range of from 400 to 40 $m^2/g$ are preferred, and ultrafine inorganic particles having an average particle of from 0.005 to 0.05 μm, and having a specific surface area within the range of from 200 to 50 $m^2/g$, or ultrafine inorganic particles having an average particle size within the range of from 0.01 to 0.04 μm, and having a specific surface area within the range of from 400 to 40 $m^2/g$ are more preferred, and ultrafine inorganic particles having an average particle size within the range of from 0.01 to 0.04 μm, and having a specific surface area within the range of from 200 to 50 $m^2/g$ are even more preferred. The ultrafine inorganic particles as such are referred to as so-called nanoparticles (ultrafine particle filler), which can give a dental mill blank having more excellent transparency and abrasion gloss. The content of the ultrafine inorganic particles in a case where the above-mentioned ultrafine inorganic particles are applied is preferably 90% by weight or more, more preferably 95% by weight or more, and even more preferably substantially 100% by weight, of the inorganic filler.

As the above nanoparticles, known ultrafine inorganic particles that are used in dental composite resins etc. are used without any limitations. Preferably, the nanoparticles include inorganic oxide particles such as particles of silica, alumina, titania, or zirconia, or composite oxide particles made from these inorganic oxide particles, particles of calcium phosphate, hydroxyapatite, yttrium fluoride, ytterbium fluoride, barium titanate, potassium titanate, etc. Preferably, the nanoparticles are particles made of silica, alumina, titania, silica/alumina composite oxide, silica/zirconia composite oxide, prepared by flame pyrolysis, including, for example, Aerosil (registered trademark) OX-50, Aerosil (registered trademark) 50, Aerosil (registered trademark) 130, Aerosil (registered trademark) 200, Aerosil (registered trademark) 380, Aerosil (registered trademark) MOX80, Aerosil (registered trademark) R972, Aerosil (registered trademark) RY50, AEROXIDE (registered trademark) Alu C, AEROXIDE (registered trademark) $TiO_2P25$, AEROXIDE (registered trademark) $TiO_2P25S$, VP Zirconium Oxide 3-YSZ, VP Zirconium Oxide 3-YSZ PH, each being manufactured by Nippon Aerosil Co., Ltd. In addition, the shape of the ultrafine inorganic particles is not particularly limited, and can be appropriately selected and used.

In general, in dental composite resins, it would be difficult to increase the content of inorganic particles as the particle size of the inorganic particles to be blended becomes small, and especially when a ultrafine particle filler as mentioned above is blended, the tendency becomes marked. If a polymerizable monomer and an ultrafine particle filler are mixed to try to give a paste-like composite resin, the content of the ultrafine particle filler is at most 60% by weight or so, and it was difficult to actually blend the ultrafine particle filler at a content of 65% by weight or more. However, by employing the method of the present invention, a mill blank having a filled amount of 65% by weight or more can be easily obtained. As such, a mill blank containing ultrafine particle filler at a content of 65% by weight or more is one of the preferred embodiments in the present invention. When the above-mentioned ultrafine particle filler is used, the content of the inorganic filler is preferably 65% by weight or more, more preferably 70% by weight or more, and even more preferably 75% by weight or more, and preferably 95% by weight or less, more preferably 90% by weight or less, and even more preferably 88% by weight or less, of the dental mill blank in the present invention. In addition, the content is within the range of preferably from 65 to 95% by weight, more preferably from 70 to 90% by weight, and even more preferably from 70 to 88% by weight.

Furthermore, aggregated particles obtained by aggregating the above-mentioned ultrafine particle filler (nanoparticles) can also be suitably used in the present invention. Especially, in a case where the particle sizes of the aggregated particles are within the range of from 1 to 20 μm, and preferably from 2 to 10 μm, a mill blank having excellent mechanical strength can be provided. Therefore, in one of another preferred embodiments of the present invention, it is preferable that an inorganic filler is aggregated particles obtained by aggregating ultrafine inorganic particles having an average particle size within the range of from 0.001 to 0.1 μm, and a specific surface area within the range of from 500 to 30 m$^2$/g, and that the inorganic filler contains inorganic particles in which the average particle size of the aggregated particles is from 1 to 20 μm. When the above-mentioned aggregated particles are applied, the content of the aggregated particles is preferably 90% by weight or more, more preferably 95% by weight or more, and even more preferably substantially 100% by weight, of the inorganic filler. Here, the average particle size of the aggregated particles refers to a particle size measured with a laser diffraction particle size distribution analyzer (SALD-2100, manufactured by Shimadzu Corporation) using a 0.2% aqueous sodium hexametaphosphate as a dispersion medium.

Usually, a commercially available ultrafine particle filler is present as aggregates, but 10 mg of an inorganic oxide powder is added to water or water added with a surfactant such as sodium hexametaphosphate in an amount of 5% by weight or less (dispersion medium), and the mixture is then subjected to dispersion treatment for 30 minutes at an ultrasonic strength of an output power of 40 W and frequency of 39 KHz. Therefore, the aggregates are dispersed to particle sizes indicated by the manufacturer, so that the dispersed aggregates only have a weak aggregating force. However, the aggregated particles in the present invention show those in which the particles themselves are firmly aggregated, and the aggregated particles undergo hardly any dispersion even under the above conditions. As the ultrafine particle filler constituting the aggregated particles, known ultrafine particle fillers that are used in dental curable compositions etc. can be used without any limitations, so long as the filler has an average particle size of from 0.001 to 0.1 μm. Preferably, the ultrafine particle filler includes inorganic oxide particles of silica, alumina, titania, zirconia, etc., composite oxide particles made of these inorganic oxides, particles of calcium phosphate, hydroxyapatite, yttrium fluoride, ytterbium fluoride, etc. These inorganic particles can be used alone or in a combination of two or more kinds.

As a method for preparing an aggregated filler used in the present invention from a commercially available ultrafine particle filler, a method including heating a filler to near a temperature immediately before the filler is melted to an extent that the contacted fillers themselves are slightly fused is suitably used, in order to further increase its aggregating force. In addition, in this case, in order to control the shape of the aggregated filler, the filler may be previously made into aggregated form prior to heating. For example, a method includes a method including placing a filler in an appropriate container and applying pressure thereto, or once dispersing a filler in a solvent, and subjecting the dispersion to spray-drying or the like, thereby removing the solvent.

In addition, another preferred methods for preparing an aggregate of ultrafine particle filler include using a silica sol, an alumina sol, a titania sol, etc. prepared by a wet method, drying the sol by a method such as lyophilization or spray-drying, and optionally heat-treating the dried product, whereby aggregated particles in which particles themselves are firmly aggregated can be obtained. Specific examples of the sol include one manufactured by Nippon Shokubai Co., Ltd., trade name: Seahostar, one manufactured by JGC Catalysts and Chemicals, Ltd., trade name: OSCAL, QUEEN TITANIC, ones manufactured by Nissan Chemical Industries, Ltd., trade names: SNOWTEX, Alumina Sol, CELNAX, NanoUse, etc. The shape of the ultrafine inorganic particles is not particularly limited, and the shape can be appropriately selected and used.

Further, as the above-mentioned aggregated particles, amorphous fine inorganic oxide particles obtained by coating the surface of silica-based fine particles with a composite oxide made of at least zirconium, silicon and oxygen, as described in a patent publication Japanese Patent Laid-Open No. 2008-115136 or WO2009/133913, and, for example, the amorphous powder having an average particle size of from 1 to 20 μm can be suitably used.

In a case of using the aggregated particles, the content of the inorganic filler is within the range of preferably 65% by weight or more, more preferably 70% by weight or more, and even more preferably 75% by weight or more, and preferably 95% by weight or less, more preferably 90% by weight or less, and even more preferably 88% by weight or less, of the dental mill blank in the present invention. In addition, the content is within the range of preferably from 65 to 95% by weight, more preferably from 70 to 90% by weight, and even more preferably from 75 to 88% by weight.

In one of another preferred embodiments, as the inorganic filler, ultrafine inorganic particles having an average particle size within the range of from 0.001 to 0.1 μm and a specific surface area within the range of from 500 to 30 m$^2$/g are used together with inorganic particles having an average particle size within the range of from 0.2 to 2 μm and a particle size range of from 0.1 to 10 μm. As such, a composition prepared by blending (mixing) both of the ultrafine inorganic particles and inorganic particles of from 0.2 to 2 μm is referred to as hybrid inorganic particles, which can give a dental mill blank having more excellent mechanical strength. In a case where the above-mentioned hybrid inorganic particles are applied, the content of the hybrid inorganic particles is preferably 90% by weight or more, more preferably 95% by weight or more, and even more preferably substantially 100% by weight, of the inorganic filler. Hereinafter, inorganic particles having an average particle size of from 0.2 to 2 μm and a particle size range of from 0.1 to 10 μm may be simply referred to as hybrid inorganic particles of 0.2 μm or more.

As the ultrafine inorganic particles in the hybrid inorganic particles, the same ones as those for the above-mentioned ultrafine particle filler are used. On the other hand, the inorganic particles of 0.2 μm or more to be blended with the ultrafine particle filler are inorganic particles having an average particle size within the range of preferably 0.2 μm or more, and more preferably 0.4 μm or more, and of preferably 2 μm or less, and more preferably 1.5 μm or less, and a particle size range of preferably within the range of 0.1

μm or more, and of preferably 10 μm or less, and more preferably 5.0 μm or less, or inorganic particles having an average particle size of preferably from 0.2 to 2 μm, and more preferably from 0.4 to 1.5 μm, and a particle size range of preferably from 0.1 to 10 μm, and more preferably from 0.1 to 5.0 μm. In this embodiment, inorganic particles having an average particle size and a particle size range mentioned above, the inorganic particles having a composition as exemplified by the above-mentioned submicron filler are used.

A weight ratio of the ultrafine inorganic particles and the inorganic particles of 0.2 μm or more in the hybrid inorganic particles, i.e. ultrafine inorganic particles/inorganic particles of 0.2 μm or more, is preferably from 1/1 to 1/20, and more preferably from 1/3 to 1/10.

Specific examples of the hybrid inorganic particles include the following combinations. For example, specific examples of the ultrafine particle filler include fine inorganic oxide particles of silica, alumina, zirconia, titania, etc., or fine composite oxide particles composed of these inorganic oxides. Among them, highly dispersible silica as represented by the trade name Aerosil, highly dispersible alumina, titania, or zirconia as represented by the trade name AEROXIDE are more preferred. In addition, as the hybrid inorganic particles of 0.2 μm or more to be used in combination therewith, barium-boroaluminosilicate glass, lanthanum glass, strontium-boroaluminosilicate glass, feldspar, mullite, quartz, Pyrex (registered trademark) glass, silica glass, etc., which are previously exemplified, can be suitably used.

In a case where the inorganic particles having a hybrid inorganic particles are used as mentioned above, the content of the inorganic filler is within the range of preferably 80% by weight or more, more preferably 85% by weight or more, and even more preferably 88% by weight or more, and preferably 96% by weight or less, and more preferably 95% by weight or less, of the dental mill blank according to the present invention. In addition, the content is within the range of preferably from 80 to 96% by weight, more preferably from 85 to 95% by weight, and even more preferably from 88 to 95% by weight. The content of the inorganic particles as used herein refers to a total content of the ultrafine inorganic particles and the hybrid inorganic particles of 0.2 μm or more in the hybrid inorganic particles.

In one of still another preferred embodiments, in the method for producing a dental mill blank of the present invention, two or more kinds of different inorganic particles, or identical inorganic particles, are subjected to press molding in a layered form separately, whereby a mill blank having a layered structure having different physical properties, transparency, tone, etc. can be produced. The dental mill blank having a layered structure as such can give a dental prosthesis that is clinically useful. For example, if inorganic particles in which transparency of a cured product is adjusted to be increased are arranged in a first layer and inorganic particles of which tone is adjusted to ivory color are arranged in a second layer, in a crown obtained by machining the mill blank, a crown being excellent in aesthetic properties, having an enamel color in an upper layer and a dentine color in a lower layer, can be produced.

A method for preparing inorganic particles having different tones or transparency as described above can be carried out by, for example, mixing and dispersing a pigment (colored particles) in the inorganic particles. As the pigment, known pigments that are usable in dental compositions are used without any limitations. The pigment may be any of inorganic pigments and/or organic pigments. The inorganic pigment includes, for example, chromates such as chromium yellow, zinc yellow, and barium yellow; ferrocyanides such as iron blue; sulfides such as vermilion, cadmium yellow, zinc sulfide, antimony white, and cadmium red; sulfates such as barium sulfate, zinc sulfate, strontium sulfate; oxides such as zinc flower, titanium white, red oxide, black iron, and chromium oxide; hydroxides such as aluminum hydroxide; silicates such as calcium silicate and lapis lazuli; carbons such as carbon black and graphite; etc. The organic pigment includes, for example, nitroso-based pigments such as Naphthol Green B and Naphthol Green Y; nitro-based pigments such as Naphthol S, Lithol Fast Yellow 2G; insoluble azo-based pigments such as Permanent Red 4R, Brilliant Fast Scarlet, Hansa Yellow, and Benzidine Yellow; hardly soluble azo-based pigments such as Lithol Red, Lake Red C, and Lake Red D; soluble azo-based pigments such as Brilliant Carmine 6B, Permanent Red FSR, Pigment Scarlet 3B, and Bordeaux 10B, phthalocyanine-based pigments such as Phthalocyanine Blue, Phthalocyanine Green, and Sky Blue; basic dye-based pigments such as Rhodamine Lake, Malachite Green Lake, and Methyl Violet Lake; acidic dye-based pigments such as Peacock Blue Lake, eosin lake, and Quinoline Yellow Lake, etc. These pigments can be used alone or in combinations of two or more kinds, which can be properly selected depending upon the tones to be intended for the mill blank. Among these pigments, dispensary Titanium Oxide White, red oxide, iron black, yellow iron oxide, etc., which are inorganic pigments having excellent heat resistance, light resistance, etc. are preferred in the dental mill blank of the present invention.

The content of the pigment is not particularly limited because the pigment is properly adjusted depending upon the desired tone, and the content of the pigment is preferably 0.000001 parts by weight or more, and more preferably 0.00001 parts by weight or more, and preferably 5 parts by weight or less, and more preferably 1 part by weight or less, based on 100 parts by weight of the inorganic particles in the layer in which the pigment is blended. In addition, the content is preferably from 0.000001 to 5 parts by weight, and more preferably from 0.00001 to 1 part by weight.

As to the method for homogeneously mixing and dispersing inorganic particles and a pigment, known powder mixing and dispersion methods are used without particular limitations, which may be any one of dry methods or wet methods. However, in order to even more homogeneously mixing and dispersing each of the particles, a method including dispersing both the powders in the presence of a solvent, and thereafter removing or distilling off the solvent is preferred. The dispersion can be carried out by employing known methods in the art. For example, a dispersing machine such as a sand-mill, a beads-mill, an attritor, a colloidal mill, a ball-mill, a ultrasonic disruptor, a homo mixer, a dissolver, or a homogenizer can be used. The dispersion conditions may differ depending upon sizes of the particle sizes and amounts charged of the inorganic particle powder and the pigment, kinds and amount of the solvents, kinds of the dispersing machines, etc. The dispersion conditions such as dispersion time, stirring tools, and rotational speeds can be properly selected in accordance with the dispersion states. As the solvent used in the wet dispersion, water and/or a solvent compatible with water is preferred, and an alcohol including, e.g. ethanol, methanol, or isopropanol, an ether, a ketone, e.g. acetone, methyl ethyl ketone, etc. can be used as the solvent.

In addition, as a method for adjusting a color tone, in addition to a method according to pigment dispersion as mentioned above, those inorganic particles having a color in the material itself may be used, such as the colored glass. Examples where the inorganic particles themselves are colored as such include powders obtained by optionally pulverizing commercially available porcelain powders, e.g. ones manufactured by VITA under the trade names: VM, VM7, ones commercially available from KURARAY NORITAKE DENTAL INC. under the trade names of Noritake Super Porcelain AAA, CERABIEN ZR, and the like, to adjust the particle sizes of the pulverized powders.

In addition, as a method for adjusting transparency of each of the layers, a method of adjusting refractive indexes and particle sizes of the inorganic particles is also suitably used. In general, it has been known that as to the transparency of the resin in which inorganic particles are dispersed, the smaller the difference in refractive indexes between the inorganic particles and the resin, and the further away the particle sizes from the wavelength of the visible light, i.e. from 0.4 to 0.7 µm, the higher the transparency. Therefore, as the inorganic powder to be arranged in a layer having high transparency, an inorganic powder having a refractive index that closely approximates a refractive index as much as possible of the immersed polymerizable monomer after curing is selected, or a refractive index of a polymerizable monomer is adjusted so as to match the refractive index of the inorganic powder.

Furthermore, inorganic particles having excellent gloss can be arranged in an enamel colored layer, and inorganic particles having excellent mechanical strength can be arranged in a dentine colored layer, which is an inner layer. The above combination can give a clinically very useful crown prosthesis which has excellent durability in the oral cavity.

Preferred inorganic particles for each of the layers in combination are as follows. Specifically, as inorganic particles in the enamel colored layer, the same ones as those in the ultrafine particle filler and the submicron filler mentioned above are used. On the other hand, as the inorganic particles in the dentine colored layer, the same ones as those in the submicron filler, the aggregated particles of the ultrafine particle filler and the hybrid inorganic particles mentioned above are used. For example, embodiments include an embodiment where an ultrafine particle filler is used in an enamel color layer, and a submicron filler is used in a dentine colored layer, and an embodiment where a submicron filler is used in an enamel colored layer, and fine hybrid inorganic particles are used in a dentine colored layer.

When the inorganic particles are subjected to press molding to a layered form, the content of the inorganic filler is within the range of preferably 60% by weight or more, more preferably 65% by weight or more, and even more preferably 70% by weight or more, and preferably 96% by weight or less, more preferably 94% by weight or less, and even more preferably 92% by weight or less, of the dental mill blank according to the present invention. In addition, the content is within the range of preferably from 60 to 96% by weight, more preferably from 65 to 96% by weight, even more preferably from 70 to 94% by weight, and even more preferably from 70 to 92% by weight. Here, the content of the inorganic filler as referred to herein is a content totaling the inorganic particles in all the layers.

In addition, in the present invention, as an inorganic filler, inorganic particles previously subjected to surface treatment can be used. By subjecting to surface treatment, the mechanical strength of the resulting mill blank is improved. In addition, when the aggregate of the inorganic particles, i.e. an inorganic filler molded article, obtained by subjecting an inorganic filler to a press molding is contacted with a polymerizable monomer described later to allow the polymerizable monomer to infiltrate into the interstitials of the aggregation of the inorganic particles, there are some advantageous merits that the compatibility between the inorganic particle surface and the polymerizable monomer becomes excellent, so that the polymerizable monomer is more likely to infiltrate into the interstitials between the aggregates. Here, in a case where hybrid inorganic particles are subjected to a surface treatment, each of the ultrafine inorganic particles and the hybrid inorganic particles of 0.2 µm or more in the hybrid inorganic particles may be subjected to a surface treatment, and then mixed to give hybrid inorganic particles, or alternatively a mixture of the ultrafine inorganic particles and the inorganic particles of 0.2 µm or more may be subjected to a surface treatment.

As the surface treating agent, a known surface treating agent can be used, and an organometallic compound such as an organosilicon compound, an organotitanium compound, an organozirconium compound, or an organoaluminum compound, or an acidic group-containing organic compound having at least one acidic group, such as a phosphoric acid group, a pyrophosphoric acid group, a thiophosphoric acid group, a phosphonic acid group, a sulfonic acid group, or a carboxylic acid group, can be used. When two or more kinds of surface treating agents are used, a surface-treated layer of a mixture of the two or more kinds of surface-treating agents may be formed or surface-treated layers of a multi-layered structure in which a plurality of surface-treated layers are laminated may be formed. Also, as a method for surface treatment, a known method can be used without particular limitations.

The organosilicon compound includes a compound represented by $R^1{}_n SiX_{4-n}$, wherein $R^1$ is a substituted or unsubstituted hydrocarbon group having from 1 to 12 carbon atoms, X is an alkoxy group having from 1 to 4 carbon atoms, an acetoxy group, a hydroxyl group, a halogen atom, or a hydrogen atom, and n is an integer of from 0 to 3, with proviso that in a case where there are plural $R^1$'s and X's, each of R's and X's may be identical or different.

Specific examples include, for example, methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(β-methoxyethoxy)silane, 3,3,3-trifluoropropyltrimethoxysilane, methyl-3,3,3-trifluoropropyldimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropylmethyldiethoxysilane, N-β-(aminoethyl)-γ-aminopropylmethyldimethoxysilane, N-(β-(aminoethyl)-γ-aminopropyltrimethoxysilane, N-β-(aminoethyl)-γ-aminopropyltriethoxysilane, γ-aminopropyltriethoxysilane, γ-aminopropyltrimethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyltrimethoxysilane [having from 3 to 12 carbon atoms between a (meth)acryloxy group and a silicon atom, e.g., γ-methacryloxypropyltrimethoxysilane, etc.], ω-(meth)acryloxyalkyltriethoxysilane [having from 3 to 12 carbon atoms between a (meth)acryloxy group and a silicon atom, e.g., γ-methacryloxypropyltriethoxysilane, etc.], etc. Here, in the present invention, the expression "(meth)acryloxy" is used in the meaning of embracing both methacryloxy and acryloxy.

Among them, a coupling agent having a functional group copolymerizable with a polymerizable monomer, for example, ω-(meth)acryloxyalkyltrimethoxysilane [having from 3 to 12 carbon atoms between a (meth)acryloxy group and a silicon atom], ω-(meth)acryloxyalkyltriethoxysilane [having from 3 to 12 carbon atoms between a (meth)acryloxy group and a silicon atom], vinyltrimethoxysilane, vinyltriethoxysilane, vinyltriacetoxysilane, γ-glycidoxypropyltrimethoxysilane, etc. is preferably used.

The organotitanium compound includes, for example, tetramethyl titanate, tetraisopropyl titanate, tetra-n-butyl titanate, butyl titanate dimer, tetra(2-ethylhexyl) titanate, etc.

The organozirconium compound includes, for example, zirconium isopropoxide, zirconium n-butoxide, zirconium acetylacetonate, zirconium acetate, etc.

The organoaluminum compound includes, for example, aluminum acetylacetonate, a chelating compound of a salt of aluminum and an organic acid.

The acidic group-containing organic compound containing a phosphoric acid group includes 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, ammonium salts thereof, etc.

In addition, as the acidic group-containing organic compound having an acidic group such as a pyrophosphoric acid group, a thiophosphoric acid group, a phosphonic acid group, a sulfonic acid group, or a carboxylic acid group, the compounds listed in, for example, WO 2012/042911 can be suitably used.

The above-mentioned surface-treating agent may be used alone, or in a combination of plural kinds. In addition, in order to increase chemical bondability between the inorganic filler and the polymerizable monomer so as to enhance the mechanical strength of the cured product, it is more preferable to use an acidic group-containing organic compound having a functional group copolymerizable with the polymerizable monomer.

The amount of the surface-treating agent used is not particularly limited, and it is preferable that the amount used is, for example from 0.1 to 50 parts by weight, based on 100 parts by weight of the inorganic filler.

As to a method for subjecting the inorganic filler to press molding, a known method is used without limitations. For example, a method including filling an inorganic filler in a mold for press (die) of a desired size, and applying a pressure according to uniaxial press using an upper punch and a lower punch is preferred. The press pressure at this time is set appropriately to an optimal value depending upon the sizes of the intended molded articles, and the kinds and particle sizes of the inorganic particles, and the press pressure is usually 10 MPa or more. When the press pressure is low, the inorganic particles are not densely filled, so that the interstitials of the inorganic particles are not sufficiently narrowed, whereby the inorganic particle content per unit volume cannot be increased in the mill blank obtained. As a result, mechanical strength, abrasion resistance, and surface gloss of a dental prosthesis obtained from the mill blank may be insufficient. It is preferable that the higher the press pressure the better, from this viewpoint. However, in consideration of the aspect of the sizes of the press molded article and productivity such as facility factors, the press pressure according to uniaxial press is within the range of usually 200 MPa or less, and preferably 10 MPa or more, more preferably 20 MPa or more, and even more preferably 25 MPa or more, and preferably 180 MPa or less, more preferably 150 MPa or less, even more preferably 100 MPa or less, and still even more preferably 80 MPa or less. In addition, the press pressure is preferably within the range of from 10 to 200 MPa, more preferably from 20 to 100 MPa, even more preferably from 25 to 80 MPa. The press time can be appropriately set depending upon the press pressure, and the press time is usually from 1 to 120 minutes.

In addition, as a method for press molding in the method of the present invention, it is preferable that the method is a cold isotactic press (CIP) step, and/or includes a CIP step. Specifically, it is preferable that press molding is carried out with a CIP step without performing the above-mentioned uniaxial press, or in the alternative, the press molding is carried out with the above-mentioned uniaxial press to give a molded article, and thereafter the molded article is further subjected to a CIP molding. In the CIP molding, usually, a press pressure higher than that of the uniaxial press can be applied, and pressure can be evenly applied from 3-dimensional directions against the molded article, fine voids undesirably formed in the inner portion of the molded article and unevenness of the aggregated state of the inorganic particles are overcome, and compression density of the inorganic particles is further increased, whereby a mill blank having a very high content of the inorganic particles is obtained. In a case where the press molding is a CIP step, an inorganic filler is filled in a container rich in flexibility such as silicon rubber or polyisoprene rubber, without going through a step of uniaxial pressing with a die, and subjecting the content to a CIP treatment in that state or in a vacuum state, whereby a press molded article can also be obtained. The applied pressure during the CIP molding is also desired to be higher. Alternatively, in a case where a molded product after the press molding with the uniaxial press is further subjected to a CIP molding, the press molded article can be subjected to a CIP treatment in that state or in a vacuum state. In the CIP treatment, for example, a CIP apparatus capable of applying pressure of 1,000 MPa or so, manufactured by Kobe Steel Ltd. can be used. It is preferable that the applied pressure during the CIP molding is higher, regardless of the presence or absence of the uniaxial press. However, in consideration of productivity, when uniaxial press is carried out, the applied pressure is within the range of preferably 30 MPa or more, more preferably 50 MPa or more, and even more preferably 100 MPa or more, and preferably 500 MPa or less, more preferably 400 MPa or less, and even more preferably 300 MPa or less. In addition, the applied pressure is preferably from 30 to 500 MPa, more preferably from 50 to 500 MPa, and even more preferably from 100 to 300 MPa. In addition, in a case where the CIP treatment is carried out without performing the uniaxial press, the applied pressure is within the range of preferably 30 MPa or more, more preferably 50 MPa or more, and even more preferably 100 MPa or more, and preferably 1,000 MPa or less, more preferably 800 MPa or less, and even more preferably 700 MPa or less. In addition, the applied pressure is preferably from 30 to 1,000 MPa, more preferably from 50 to 800 MPa, and even more preferably from 100 to 700 MPa. The CIP molding time can be appropriately set depending upon the press pressure, and the CIP molding time is usually from 1 to 60 minutes.

In addition, a method of laminating two or more kinds of different inorganic particles and subjecting the laminate to press molding includes the following method. For example, there is included a method in which a first inorganic particle powder is filled into a mold for uniaxial press (die) fitted with a lower punch, and an upper punch is set over the mold to press the powder. Next, the upper punch is removed, a second inorganic powder is filled over a pressed first inorganic powder aggregate, and the upper punch is set again, so that the second inorganic powder is pressed. Thereafter, a press molded article is taken out from the mold, whereby a press molded article in which the first inorganic particles and the second inorganic particles are laminated in a layered form can be obtained. Here, the press pressure during the above-mentioned press is appropriately set to an optimal value depending upon the kinds and the amounts of the inorganic particles used, and the press pressure in each layer may be different or the same. Also, a first inorganic powder is filled into a mold, and then evenly spread over the surface but not subjected to a press, a second inorganic powder is filled over the evenly spread surface, and the first inorganic powder and the second inorganic powder can be pressed together.

Thus, a press molded article of an inorganic filler is obtained, and the molded article can be processed to dental mill blanks of various shapes mentioned below, so that the sizes thereof are not particularly limited. Here, as the inorganic filler molded article according to the present invention, an inorganic filler which is subjected to press molding at one time may be directly used as a molded article, or inorganic fillers that are separately molded are laminated, and the laminate is then subjected to press molding to give a single molded article, or a new inorganic filler is subjected to press molding onto a molded article formed separately, thereby forming a single molded article.

The molded article in which the inorganic filler is aggregated, obtained as such, is allowed to contact with a polymerizable monomer described later, thereby infiltrating the polymerizable monomer into the interstitials of the powdery primary particles, whereby consequently a composition having a structure in which the inorganic particles are very densely dispersed in a polymerizable monomer would be obtained. Therefore, in the present invention, it is preferable to use an inorganic filler in a state that is subjected to press molding, and as mentioned above, for example, a porous member being communicated by fitting, as in Patent Publication 6, is not preferred. Specifically, a molded article made of a highly dense filler of an inorganic filler is preferred.

In addition, in general, in a particle-dispersible composite material as described in the present invention, the smaller the particle sizes of the inorganic particles dispersed in the resin, the more excellent the abrasion gloss, and a crown restorative material of which gloss can be maintained for a long period of time in the oral cavity is obtained. On the other hand, as the particle size of the inorganic particles becomes smaller, it would be difficult to fill the inorganic particles in the composite material in a high density, thereby having a tendency of lowering mechanical strength and abrasion resistance of a cured product. However, in the present invention, a dental mill blank is produced by subjecting an inorganic filler to press molding, so that high-density filling is made possible even when the particle sizes of the inorganic particles are small, whereby a dental prosthesis obtained from the mill blank has excellent gloss and improved strength and abrasion resistance.

The content of the inorganic filler in the dental mill blank obtained according to the present invention varies depending upon the particle sizes and shapes of the inorganic particles used, and even when inorganic particles having small particle sizes are used, the inorganic filler is usually blended in an amount of 60% by weight or more, preferably 70% by weight or more, more preferably 80% by weight or more, even more preferably 82% by weight or more, and even more preferably 85% by weight or more, and preferably 96% by weight or less, and more preferably 95% or weight or less. In addition, the content is preferably from 60 to 96% by weight, more preferably from 70 to 96% by weight, even more preferably from 80 to 95% by weight, and even more preferably from 85 to 95% by weight. Here, the inorganic filler content as referred to herein is a value measured by ignition residue of a cured product.

In the measurement of the ignition residue of a cured product, specifically, the ignition residue can be calculated by, for example, placing a cured product in a crucible and heating the content in an electric furnace at a temperature of 575° C. for a given period of time, thereby burning away an organic resin component, and measuring the weight of the residual inorganic particles. In this method, in a case of a mill blank obtained by using inorganic particles subjected to a surface treatment, it is to be noted that a surface treating agent used in the treatment would be calculated as a burned organic resin component.

Next, the molded article made of the inorganic filler thus obtained, i.e. the inorganic filler molded article, is allowed to contact with a composition containing a polymerizable monomer, i.e. a polymerizable monomer-containing composition.

The polymerizable monomer-containing composition contains the following polymerizable monomers.

As the polymerizable monomer usable in the present invention, a known polymerizable monomer which is used in a dental composite resin or the like is suitably used without any limitations. In general, a radical polymerizable monomer is suitably used. Specific examples of the radical polymerizable monomer include esters of α-cyanoacrylic acid, (meth)acrylic acid, α-halogenated acrylic acid, crotonic acid, cinnamic acid, sorbic acid, maleic acid, itaconic acid, etc., (meth)acrylamide, (meth)acrylamide derivatives, vinyl esters, vinyl ethers, mono-N-vinyl derivatives, styrene derivatives, etc. Among them, (meth)acrylate esters and (meth)acrylamide derivatives are preferred, and (meth)acrylate esters are more preferred. Here, in the present invention, the expression "(meth)acryl" is used in the meaning of embracing both methacryl and acryl.

Examples of (meth)acrylate ester-based and (meth)acrylamide derivative-based polymerizable monomers are given hereinbelow.

(I) Monofunctional (meth)acrylates and (meth)acrylamide derivatives include:

methyl (meth)acrylate, isobutyl (meth)acrylate, benzyl (meth)acrylate, lauryl (meth)acrylate, 2-(N,N-dimethylamino)ethyl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N-(dihydroxyethyl) (meth)acrylamide, (meth)acryloyloxydodecylpyridinium bromide, (meth)acryloyloxydodecylpyridinium chloride, (meth)acryloyloxyhexadecylpyridinium chloride, (meth) acryloyloxydecylammonium chloride, 10-mercaptodecyl (meth)acrylate, etc.

(II) Bifunctional (meth)acrylates Include:

ethylene glycol di(meth)acrylate, triethylene glycol di(meth)acrylate, propylene glycol di(meth)acrylate, neopentyl glycol di(meth)acrylate, 1,6-hexanediol di(meth) acrylate, 1,10-decanediol di(meth)acrylate, bisphenol A diglycidyl (meth)acrylate (2,2-bis[4-[3-(meth)acryloyloxy-2-hydroxypropoxy]phenyl]propane (commonly known as BisGMA)), 2,2-bis[4-(meth)acryloyloxyethoxyphenyl]propane, 2,2-bis[4-(meth)acryloyloxypolyethoxyphenyl]propane, 1,2-bis[3-(meth)acryloyloxy-2-hydroxypropoxy]ethane, pentaerythritol di(meth)acrylate, [2,2,4-trimethylhexamethylenebis(2-carbamoyloxyethyl)] dimethacrylate (commonly known as UDMA), 2,2,3,3,4,4-hexafluoro-1,5-pentyl dimethacrylate, tricyclodecanedimethanol di(meth)acrylate, etc.

(III) Trifunctional or higher polyfunctional (meth)acrylates include:

trimethylolpropane tri(meth)acrylate, trimethylolethane tri(meth)acrylate, tetramethylolmethane tri(meth)acrylate, pentaerythritol tetra(meth)acrylate, dipentaerythritol hexa (meth)acrylate, N,N'-(2,2,4-trimethylhexamethylene)bis[2-(aminocarboxy)propane-1,3-diol]tetramethacrylate, 1,7-diacryloyloxy-2,2,6,6-tetraacryloyloxymethyl-4-oxyheptane, etc.

In addition, besides these (meth)acrylate ester-based and (meth)acrylamide derivative-based polymerizable monomers, oxysilane compounds and oxetane compounds, which are cation-polymerizable, are also preferably used.

Any of the above-mentioned polymerizable monomers can be used alone or in admixture of two or more kinds. Also, it is preferable that the polymerizable monomer usable in the present invention is in a liquid state, but the polymerizable monomer does not necessarily need to be in a liquid state at an ambient temperature, so long as the polymerizable monomer is a liquid under the environment of the step of allowing the polymerizable monomer to contact with a powdery press molded article. Further, even when the polymerizable monomer is in a solid form, the polymerizable monomer can be used by mixing with other liquid polymerizable monomers to dissolve.

The preferred viscosity range at 25° C. of the polymerizable monomer is 10 Pa·s or less, more preferably 5 Pa·s or less, and even more preferably 2 Pa·s or less. When two or more kinds of the polymerizable monomers are mixed to dissolve, or further diluted with a solvent, it is preferable that the viscosity of the above-mentioned polymerizable monomer in a state of a composition prepared by mixing the polymerizable monomers to dissolve upon use is within the viscosity range, but individual polymerizable monomers do not necessarily need to be within the viscosity range.

The content of the polymerizable monomer in the dental mill blank can be properly adjusted depending upon a degree of contact with a polymerizable monomer-containing composition. In addition, in the dental mill blank of the present invention, the content of the polymerizable monomer cannot be unconditionally determined, because the content of the inorganic filler fluctuates depending upon the average particle size of the inorganic particles constituting the inorganic filler or the method of press molding.

The dental mill blank of the present invention is produced by allowing a polymerizable monomer immersed in the interstitials of an internal of an inorganic filler molded article to polymerize and cure. Therefore, the polymerizable monomer-containing composition may contain a polymerization initiator to facilitate the polymerization curing. The polymerization initiator can be selected from polymerization initiators used in the general industrial fields, and used. Among them, polymerization initiators which are usable in dental applications are preferably used, and polymerization initiators for thermal polymerization, photopolymerization and chemical polymerization can be used alone or properly in combinations of two or more kinds.

The thermal polymerization initiator includes organic peroxides and azo compounds, etc.

Examples of the organic peroxides usable as the above-mentioned thermal polymerization initiator include ketone peroxides, hydroperoxides, diacyl peroxides, dialkyl peroxides, peroxyketals, peroxyesters, peroxydicarbonates, etc.

The ketone peroxides usable as the above-mentioned thermal polymerization initiator include methyl ethyl ketone peroxide, methyl isobutyl ketone peroxide, methyl cyclohexanone peroxide, cyclohexanone peroxide, etc.

The hydroperoxides usable as the above-mentioned thermal polymerization initiator include 2,5-dimethylhexane-2, 5-dihydroperoxide, diisopropylbenzene hydroperoxide, cumene hydroperoxide, t-butyl hydroperoxide, and 1,1,3,3-tetramethylbutyl hydroperoxide, etc.

The diacyl peroxides usable as the above-mentioned thermal polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide, etc.

The dialkyl peroxides usable as the above-mentioned thermal polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl) benzene, and 2,5-dimethyl-2,5-di(t-butylperoxy)-3-hexyne, etc.

The peroxyketals usable as the above-mentioned thermal polymerization initiator include 1,1-bis(t-butylperoxy)-3,3, 5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester, etc.

The peroxyesters usable as the above-mentioned thermal polymerization initiator include α-cumyl peroxyneodecanoate, t-butyl peroxyneodecanoate, t-butyl peroxypivalate, 2,2, 4-trimethylpentyl peroxy-2-ethyl hexanoate, t-amyl peroxy-2-ethyl hexanoate, t-butyl peroxy-2-ethyl hexanoate, di-t-butyl peroxyisophthalate, di-t-butyl peroxyhexahydroterephthalate, t-butyl peroxy-3,3,5-trimethyl hexanoate, t-butyl peroxyacetate, t-butyl peroxybenzoate, and t-butyl peroxymaleic acid, etc.

The peroxydicarbonates usable as the above-mentioned thermal polymerization initiator include di-3-methoxy peroxydicarbonate, di-2-ethylhexyl peroxydicarbonate, bis(4-t-butylcyclohexyl) peroxydicarbonate, diisopropyl peroxydicarbonate, di-n-propyl peroxydicarbonate, di-2-ethoxyethyl peroxydicarbonate, and diallyl peroxydicarbonate, etc.

Among these organic peroxides, diacyl peroxides are preferably used, from an overall balance of safety, storage stability, radical formation ability, among which benzoyl peroxide is more preferably used.

The azo compounds usable as the above-mentioned thermal polymerization initiator include 2,2-azobisisobutyronitrile, 2,2-azobis-2,4-dimethylvaleronitrile, 4,4-azobis-4-cyanovaleric acid, 1,1-azobis-1-cyclohexanecarbonitrile, dimethyl-2,2-azobisisobutyrate, 2,2-azobis(2-aminopropane)dihydrochloride, etc.

The photopolymerization initiators include (bis)acylphosphine oxides, α-diketones, coumarins, etc.

Among the (bis)acyphosphine oxides usable as the above-mentioned photopolymerization initiator, the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyldi-(2,6-dimethylphenyl) phosphonate, and salts thereof, etc. The bisacylphosphine oxides include bis-(2,6-dichlorobenzoyl) phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide, and salts thereof, etc.

Among these (bis)acylphosphine oxides, 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt are preferred.

The α-diketones usable as the above-mentioned photopolymerization initiator include, for example, diacetyl, dibenzyl, camphorquinone, 2,3-pentadione, 2,3-octadione, 9,10-phenanthrenequinone, 4,4'-oxybenzyl, acenaphthenequinone, etc. Among them, camphorquinone is preferred.

Examples of the coumarins usable as the above-mentioned photopolymerization initiator include compounds listed in Japanese Patent Laid-Open Nos. Hei-9-3109 and Hei-10-245525, such as 3,3'-carbonylbis(7-diethylamino) coumarin, 3-(4-methoxybenzoyl)coumarin, 3-thienoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl) coumarin, 3,5-carbonylbis (7-methoxycoumarin), 3-benzoyl-6-bromocoumarin, 3,3'-carbonylbiscoumarin, 3-benzoyl-7-dimethylaminocoumarin, 3-benzoylbenzo[f] coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f] coumarin, 7-methoxy-3-(p-nitrobenzoyl)coumarin, 3-(p-nitrobenzoyl)coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-methoxy-3 (4-methoxybenzoyl) diethylamino)coumarin, 7-methoxy-3 (4-methoxybenzoyl) coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-1,1,7,7-tetramethyl 1H,5H,11H-[1]benzopyrano[6,7,8-ij] quinolidin-11-one, and 10-(2-benzothiazoyl)-2,3,6,7-tetrahydro-1,1,7,7-tetramethyl 1H,5H,11H-[1]benzopyrano[6,7,8-ij]quinolidin-11-one.

Among the coumarin compounds mentioned above, 3,3'-carbonylbis(7-diethylaminocoumarin) and 3,3'-carbonylbis (7-dibutylaminocoumarin) are preferred.

Among these photopolymerization initiators, at least one member selected from the group consisting of the (bis) acylphosphine oxides, the α-diketones, and the coumarins which are widely used in dental curable compositions is preferably used.

In addition, the photopolymerization initiator may be able to efficiently carry out photopolymerization in a shorter period of time by further blending with a polymerization accelerator as occasion demands.

The polymerization accelerators suitable for the photopolymerization initiator include mainly tertiary amines, aldehydes, thiol group-containing compounds, sulfinic acid and/or salts thereof, etc.

Examples of the tertiary amines include, for example, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-dibutylaniline, N,N-dimethyl-3,5-di-t-dibutylaniline, N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis (2-hydroxyethyl)-3,5-dibutylaniline, n-butoxyethyl 4-dimethylaminobenzoate, (2-methacryloyloxy)ethyl 4-dimethylaminobenzoate, ethyl 4-dimethylaminobenzoate, butyl 4-dimethylaminobenzoate, N-methyldiethanolamine, 4-dimethylaminobenzophenone, trimethylamine, triethylamine, N-methyldiethanolamine, N-ethyldiethanolamine, N-n-butyldiethanolamine, N-lauryldiethanolamine, triethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, etc.

Examples of the aldehydes include dimethylaminobenzaldehyde, terephthalaldehyde, etc. Examples of the thiol group-containing compounds include 2-mercaptobenzoxazole, decanethiol, 3-mercaptopropyltrimethoxysilane, thiobenzoic acid, etc.

The sulfinic acid and salts thereof include, for example, benzenesulfinic acid, sodium benzenesulfinate, potassium benzenesulfinate, calcium benzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, calcium 2,4,6-triisopropylbenzenesulfinate, etc.

As the chemical polymerization initiator, a combination of an organic peroxide and a polymerization accelerator is preferably used. The organic peroxide usable in the chemical polymerization initiator is not limited, and a known one can be used. Specific examples include the organic peroxides exemplified in the thermal polymerization initiator mentioned above.

Among these organic peroxides, the diacyl peroxides are preferably used, from the overall balance between safety, storage stability and radical forming ability, among which benzoyl peroxide is more preferably used.

The polymerization accelerator usable in the chemical polymerization initiator can be selected from polymerization accelerators used in the general industrial fields, among which polymerization accelerators usable in dental applications are preferably used. Also, the polymerization accelerator can be used alone or in a combination of two or more kinds.

Specific examples include amines, sulfinic acid and salts thereof, copper compounds, tin compounds, etc.

The amines usable as the polymerization accelerator can be divided into aliphatic amines and aromatic amines. The aliphatic amines include, for example, primary aliphatic amines, such as n-butylamine, n-hexylamine, and n-octylamine; secondary aliphatic amines, such as diisopropylamine, dibutylamine, and N-methylethanolamine; tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine, etc.

Among them, the tertiary aliphatic amines are preferred, from the viewpoint of curing property and storage stability of the composition, among which N-methyldiethanolamine and triethanolamine are more preferably used.

In addition, the aromatic amines include, for example, N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-N,N-dimethylaminobenzoate, methyl 4-N,N-dimethylaminobenzoate, n-butoxyethyl N,N-dimethylaminobenzoate, 2-(methacryloyloxy)ethyl 4-N,N-dimethylaminobenzoate, 4-N,N-dimethylaminobenzophenone, butyl 4-dimethylaminobenzoate, etc. Among them, at least one member selected from the group consisting of N,N-di(2-hydroxyethyl)-p-toluidine, ethyl 4-N,N-dimethylaminobenzoate, n-butoxyethyl N,N-dimethylaminobenzoate, and 4-N,N-dimethylaminobenzophenone is preferably used, from the viewpoint of giving excellent curing property to the composition.

The sulfinic acid and salts thereof usable as the polymerization accelerator include, for example, p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, calcium 2,4,6-triisopropylbenzenesulfinate, etc., and sodium benzenesulfinate, sodium p-toluenesulfinate, and sodium 2,4,6-triisopropylbenzenesulfinate are preferred.

As the copper compounds usable as the polymerization accelerator, for example, copper acetylacetone, cupric acetate, copper oleate, cupric chloride, cupric bromide, etc. is preferably used.

The tin compounds usable as the polymerization accelerator include, for example, di-n-butyltin dimalate, di-n-octyltin dimalate, di-n-octyltin dilaurate, di-n-butyltin dilaurate, etc. Among them, preferred tin compounds are di-n-octyltin dilaurate and di-n-butyltin dilaurate.

Among them, it is preferable that a photopolymerization initiator and a thermal polymerization initiator are used in combination, and a combination of the (bis)acylphosphine oxide and the diacyl peroxide are more preferred.

Although the blending amount of the polymerization initiator to be blended in the polymerizable monomer-containing composition is not particularly limited, it is preferable that the polymerization initiator is contained in an amount of from 0.001 to 30 parts by weight, based on 100 parts by weight of the polymerizable monomers, from the viewpoint of curing property, etc. of the composition obtained. When the amount of the polymerization initiator blended is 0.001 parts by weight or more, the polymerization sufficiently progress, so that the composition does not have a risk of causing the lowering of mechanical strength, and the amount blended is more preferably 0.05 parts by weight or more, and even more preferably 0.1 parts by weight or more. On the other hand, when the amount of the polymerization initiator blended is 30 parts by weight or less, sufficient mechanical strength is obtained even in a case where the polymerization properties of the polymerization initiator itself are low, and further does not have a risk of causing precipitations from the composition, and the amount blended is more preferably 20 parts by weight or less.

It is possible that to the polymerizable monomer-containing composition used in the present invention is further added, in addition to the components mentioned above, a pH adjusting agent, an ultraviolet absorbent, an antioxidant, a polymerization inhibitor, a colorant, a pigment, an antibacterial agent, an X-ray contrast agent, a thickening agent, a fluorescent agent or the like, in accordance with the purposes.

The polymerizable monomer-containing composition can be prepared without particular limitations, so long as the composition contains polymerizable monomers. For example, the composition can be prepared by blending polymerizable monomers with a polymerization initiator, as occasion demands, and mixing the components.

A method for contacting a polymerizable monomer-containing composition with an inorganic filler molded article is not particularly limited, so long as the polymerizable monomer-containing composition can be infiltrated into interstitials of the inorganic particles in the inorganic filler molded article. A preferred and convenient method includes immersing the inorganic filler molded article in the polymerizable monomer-containing composition. By immersing the inorganic filler molded article, the monomers can gradually penetrate into the internal of the aggregate by capillary phenomenon. At this time, placing the surrounding environments in a reduced pressure atmosphere is a preferred means because it would accelerate the penetration of the liquid monomers. In addition, repeating the procedures of recovering to an ambient pressure after a reduced-pressure procedure, i.e. procedures of reduced pressure/ambient pressure, for plural times, is effective for shortening the time period of the step of completely penetrating the monomers into the internal of the molded article. The degree of reduced pressure at this time is properly selected depending upon the viscosities of the monomers and the particle sizes of the inorganic filler, and the degree of reduced pressure is usually within the range of 100 hecto-Pascal (hPa) (10 kPa) or less, preferably from 50 to 0.001 hPa (5 to 0.0001 kPa), and more preferably from 20 to 0.1 hPa (2 to 0.01 kPa). In addition, the degree of reduced pressure may be at vacuum ($1 \times 10^{-1}$ to $1 \times 10^{-8}$ Pa).

In addition, as the method other than immersion, a method including feeding a polymerizable monomer-containing composition, which is in a state that is subjected to press-molding with a mold, into an inorganic filler molded article in a mold, while applying pressure to the composition may also be considered. When this method is taken, it is also possible to continually carrying out the step of polymerization cure in the mold. The applied pressure conditions are preferably 2 MPa or more, more preferably 10 MPa or more, and even more preferably 20 MPa or more.

Furthermore, a method of penetrating polymerizable monomers into the internal of the inorganic filler molded article without leaving any interstitials includes a method including placing an inorganic filler molded article in which the polymerizable monomers are seemingly immersed under applied pressure conditions for a certain period of time. Specifically, it is desired that an inorganic filler molded article in which a polymerizable monomer is immersed is placed together with the polymerizable monomer under applied pressure conditions using a CIP apparatus etc. It is desired that the applied pressure conditions are preferably 20 MPa or more, more preferably 50 MPa or more, and even more preferably 100 MPa or more. Furthermore, it is even more preferable that applied pressure/ambient pressure procedures including releasing the applied pressure, recovering to an ambient pressure, and again applying pressure are repeatedly carried out.

In addition, the viscosity of the polymerizable monomer-containing composition influences the penetration rate, and it is usually the lower the viscosity, the faster the penetration. The preferred viscosity range (25° C.) is 10 Pa·s or less, more preferably 5 Pa·s or less, and even more preferably 2 Pa·s or less, and it is necessary to select the polymerizable monomer also with considering mechanical strength and refractive index besides the viscosity. Also, a method including diluting a polymerizable monomer-containing composition with a solvent to use the composition, and distilling off the solvent by the subsequent reduced pressure procedures may be employed. In addition, the temperature is raised to the range of preferably 25° C. or higher, and more preferably 30° C. or higher, and preferably 70° C. or lower, and more preferably 60° C. or lower, whereby the viscosity of the polymerizable monomer composition can be lowered, and the penetration can be accelerated.

The time for contacting a polymerizable monomer-containing composition with an inorganic filler molded article is not unconditionally determined depending upon the kinds of the inorganic filler, the size of the molded article, the level of penetration of the monomer, the contacting method, etc., and the time can be properly adjusted. For example, in a case of contacting by immersion, the time period is usually from 1 to 120 hours, and in a case of immersion under a reduced pressure, the time period is usually from 0.5 to 12 hours, and a case of contacting under applied pressure, the time period is usually from 0.2 to 6 hours.

Next, the polymerizable monomer is allowed to polymerize and cure in a state that the polymerizable monomer is infiltrated into the internal of the molded article.

The polymerization curing can be carried out by thermal polymerization and/or photopolymerization and/or chemical polymerization, and the conditions can be carried out in accordance with known methods. Among them, in the present invention, it is preferable that the polymerizable monomer is subjected to photopolymerization, and subsequently to thermal polymerization, from the viewpoint of increasing a polymerization ratio of the polymerizable monomer, thereby obtaining a mill blank having an even higher mechanical strength. The photopolymerization may be carried out with not only visible light but also UV light. In addition, upon the polymerization curing, a press molded article immersed with a polymerizable monomer is polymerized in an inert atmosphere such as nitrogen gas or under reduced-pressure environment, whereby the polymerization ratio can be increased, and the mechanical strength can be even more increased. Also, it is preferable that the molded article immersed with the polymerizable monomer is subjected to polymerization procedures in a vacuum state by packing the polymerizable monomer in a vacuum pack or the like, from the aspect of productivity. In this case, the thermal polymerization under applied pressure can be carried out with an autoclave etc.

Further, the inorganic filler molded article immersed with a polymerizable monomer is allowed to polymerize and cure while keeping the state of applied pressure. The polymerization under applied pressure as described above is a more preferred method for polymerization curing in the present invention. Specifically, an inorganic filler molded article immersed with a polymerizable monomer is placed together with the polymerizable monomer under applied pressure conditions, thereby the polymerizable monomer can penetrate even into fine interstitials of the molded article, and the remaining fine bubbles can be removed. By polymerizing the polymerizable monomer under applied pressure conditions, the mechanical strength can be even more increased. It is preferable that the applied pressure conditions are preferably 20 MPa or more, more preferably 50 MPa or more, and even more preferably 100 MPa or more. Basically, the higher the pressure, the more favorable, but actually, the pressure depends upon the ability of the pressure applying apparatus used. As the pressure applying apparatus, an autoclave, a CIP apparatus, or an HIP (hot isotactic press) apparatus is used. For example, a CIP apparatus of Kobe Steel Ltd. capable of applying pressure to 1,000 MPa or so has also been known. In addition to the thermal polymerization including raising a temperature under applied pressure conditions to polymerize the monomers, the polymerization can also be carried out by photo-polymerization or chemical polymerization. A more preferred method of polymerization under applied pressure is a method including tightly sealing a molded article immersed with a monomer with a vacuum pack in a plastic bag, a rubber tube or the like, and polymerizing the monomer while applying pressure with a CIP apparatus or the like. The higher the pressure at this time, the more favorable, and the pressure is preferably 50 MPa or more, and more preferably 200 MPa or more. Also, a method including placing a tightly sealed, monomer-immersed molded article in a CIP treatment chamber, applying a given pressure thereto, thereafter heating the treatment chamber, and beginning the polymerization under a high pressure is an even preferred polymerization method, from the viewpoint of increasing mechanical strength. For example, after applying a pressure with CIP at room temperature, a temperature is raised over a time period of from 30 minutes to 24 hours or so to reach an attaining temperature of desirably from 80° to 180° C. The polymerization time and the attaining temperature are set in consideration of the degradation temperature of the polymerization initiator to be blended to the polymerizable monomer.

Further, after allowing a polymerizable monomer to polymerize and cure, a cured product is heat-treated preferably at 80° to 150° C. for 10 to 120 minutes, thereby moderating stress strain caused in the internal of the cured product, whereby breakage of a dental prosthesis caused during machining or clinical use of the dental prosthesis can be inhibited.

Thus, according to the method of the present invention, a dental mill blank is obtained. The resulting mill blank is subjected to cutting, milling, and surface polishing to a desired size, as occasion demands, to be shipped out as a manufactured article. The dental mill blank obtainable by the present invention can realize dramatically a high level of the content of the inorganic particles in the cured product, as compared to the inorganic particle content accomplished in a conventional general dental composite resin.

In the press molded article made of inorganic particles according to the method of the present invention, it is considered that the inorganic particles are very densely filled, and that the interparticle distances of the filled particles are very short, so that the inorganic particles are considered to be basically in a contact state. On the other hand, in a dental composite resin obtainable by homogeneously mixing and kneading monomers and inorganic particles, a certain level of flowability is necessary in its paste-like state, and in the composition as such, it is necessary that the inorganic particles freely move in a medium to a certain extent, so that certain level or longer interparticle distances are needed to be secured; therefore, it is in principle nearly impossible to have a high-density filling to a level of the contact state of the inorganic particles themselves.

In the dental mill blank of the present invention having a content of the inorganic particles far above the conventional level as described above, the disadvantages pointed out in the dental prostheses fabricated from conventional dental composite resins, in other words, abrasion resistance and gloss retention etc. in the oral cavity can be remarkably improved. In addition, the highness of the content of the inorganic particles in the cured product is expected to give physical properties closer to natural dentine, in not only the improvement in mechanical strength but also coefficients of thermal expansion, hardness, etc.

In addition, when the polished smooth surface of the dental mill blank of the present invention is microscopically observed, the state in which inorganic particles are very densely filled can be observed. While a clear islands-sea structure in which inorganic particles are homogeneously dispersed in a resin matrix is observed on the abrasion surface of a cured product of a dental composite resin produced by a usual method, in the case of the mill blank of the present invention, it is observed that the inorganic particles themselves are densely filled with contacting the inorganic particles themselves, and parts of the resin matrix are very small. On the other hand, the resin matrix is homogeneously penetrated and cured in the densely filled inorganic particles, thereby making the surface of the resulting mill blank smooth, and also having excellent abrasion resistance of the opposing teeth. It is possible to indirectly deduce the content of the inorganic particles by analyzing the microscopic observation images described above according to imaging processing, and calculating the areas of the inorganic particle portion and the resin matrix portion. As the image processing system, an image analyzing software (National Institute of Health, USA, Image J) can be used.

It is desired that the size of the dental mill blank of the present invention is worked to an appropriate size so that the dental mill blank can be set to a commercially available dental CAD/CAM system. Examples of desired sizes include a rectangular pillar shape of 40 mm×20 mm×15 mm suitable in fabricating one-tooth missing bridge; a rectangular pillar shape of 17 mm×10×10 mm suitable in fabricating inlays and onlays; a rectangular pillar shape of 14 mm×18 mm×20 mm suitable in fabricating full crowns; a disk-like shape with a diameter of 100 mm and a thickness of from 10 to 28 mm suitable in fabricating long-span bridges or denture bases, etc., without being limited to these sizes.

The dental mill blank of the present invention is machined, whereby aesthetic dental prostheses having high mechanical properties and excellent abrasion resistance and gloss can be provided.

The dental prostheses produced from the mill blank of the present invention include, for example, crown restorative materials such as inlays, onlays, onlays, veneers, crowns, and bridges, abutment teeth, dental posts, dentures, denture bases, implant members (fixtures and abutments), etc. In addition, it is preferable that the machining is carried out using a commercially available dental CAD/CAM system, and examples of the CAD/CAM system include CEREC system of Sirona Dental Systems, Inc., and KATANA system of KURARAY NORITAKE DENTAL INC.

Also, the mill blank obtained according to the present invention can be used in applications other than dental applications, and the mill blank can be used in, for example, electronic material applications such as sealant materials and laminate plate molding materials, generally widely used composite material members including, for example, parts for constructions, electric appliances, household articles, and toys.

EXAMPLES

The present invention will be specifically described hereinbelow by showing Examples and Comparative Examples, without intending to limit the scope of the present invention to the following Examples.

Production Example 1 of Polymerizable Monomer-Containing Composition

Production of Polymerizable Monomer-Containing Composition

In 50 parts by weight of 2,2-bis[4-methacryloyloxypolyethoxyphenyl]propane (BisGMA) and 50 parts by weight of hexanediol dimethacrylate (HD) were dissolved 0.5 parts by weight of 2,4,6-trimethylbenzoyldiphenylphosphine oxide (TMDPO) serving as a photopolymerization initiator and 1 part by weight of benzoyl peroxide (BPO) serving as a thermal polymerization initiator, to prepare a polymerizable monomer-containing composition a.

Production Example 2 of Polymerizable Monomer-Containing Composition

Production of Polymerizable Monomer-Containing Composition

In 70 parts by weight of [2,2,4-trimethylhexamethylenebis(2-carbamoyloxyethyl)]dimethacrylate (UDMA) and 30 parts by weight of triethylene glycol dimethacrylate (TEGDMA) were dissolved 1.5 parts by weight of benzoyl peroxide serving as both a thermal polymerization initiator and a photopolymerization initiator, to prepare a polymerizable monomer-containing composition b.

Production Example 3 of Polymerizable Monomer-Containing Composition

Production of Polymerizable Monomer-Containing Composition

Thirty parts by weight of an adduct formed between 1 mol of trimethylhexamethylene diisocyanate and 2 mol of glycerol dimethacrylate (commonly known as U-4TH), 30 parts by weight of 2,2-bis[4-acryloyloxypolyethoxyphenyl]propane (the number of ethoxy groups in the molecule being 6 on average, commonly known as D6E), 25 parts by weight of neopentyl glycol dimethacrylate (commonly known as NPG), 15 parts by weight of 2,2,3,3,4,4-hexafluoro-1,5-pentyl dimethacrylate (commonly known as HFPD), and 1.5 parts by weight of azobisisobutyronitrile (commonly known as AIBN) as a polymerization initiator were mixed to dissolve, to prepare a polymerizable monomer-containing composition c.

Production Example 1 of Inorganic Particles

Production of Inorganic Powder A-1

Two-hundred grams of a commercially available barium boroaluminosilicate glass powder (manufactured by SCHOTT, GM27884, NF180, average particle size: 0.18 μm, particle size range: 0.05 to 0.50 μm, disruption form) was dispersed in 500 mL of ethanol, and 8 g of γ-methacryloxypropyltrimethoxysilane and 5 g of water were added to the dispersion, and the mixture was stirred at room temperature for 2 hours. The solvent was distilled off under a reduced pressure, and the residue was further dried at 90° C. for 3 hours, thereby surface-treating the glass powder, to give an inorganic powder A-1.

Production Example 2 of Inorganic Particles

Production of Inorganic Powder A-2

One-hundred grams of a commercially available silica-zirconia spherical filler (manufactured by Sukgyung AT Co., Ltd., average primary particle size: 0.20 μm, particle size range: from 0.05 to 0.40 μm) was surface-treated in the same manner as in Production Example 1 of Inorganic Particles with 6 g of γ-methacryloxypropyltrimethoxysilane and 3 g of water, to give a spherical inorganic powder A-2.

Production Example 3 of Inorganic Particles

Production of Inorganic Powder A-3

One-hundred grams of a commercially available ultrafine particle silica (manufactured by Nippon Aerosil Co., Ltd., Aerosil (registered trademark) OX-50, average primary particle size: 0.04 μm, BET specific surface area: 50 $m^2/g$) was surface-treated in the same manner as in Production Example 1 of Inorganic Particles with 7 g of γ-methacryloxypropyltrimethoxysilane and 5 g of water, to give a spherical inorganic powder A-3.

Production Example 4 of Inorganic Particles

Production of Inorganic Powder A-4

A commercially available silica sol (manufactured by Nissan Chemicals Industries, Ltd., average primary particle size: 10 nm, BET specific surface area: 180 $m^2/g$) was spray-dried with a spray-dryer (manufactured by Büchi, Model B290), to give an aggregated powder. This aggregated powder was spherical particles having an average particle size of 5 μm, and a particle size range within the range of from 0.5 μm to 15 μm. This aggregated powder was calcinated at 800° C. for 1 hour. Thereafter, 100 g of the powder was surface-treated in the same manner as in Production Example 1 of Inorganic Particles with 20 g of γ-methacryloxypropyltrimethoxysilane and 10 g of water, to give an inorganic powder A-4, in which inorganic ultrafine particles were aggregated.

Production Example 5 of Inorganic Particles

Production of Inorganic Powder A-5

One-hundred grams of a commercially available barium boroaluminosilicate glass powder (manufactured by SCHOTT, 8235, average particle size: 1.5 μm, particle size range: 0.1 to 5.0 μm) and 20 g of a commercially available ultrafine particle silica (manufactured by Nippon Aerosil Co., Ltd., Aerosil (registered trademark) OX-50, average primary particle size: 0.04 μm, BET specific surface area: 50 $m^2/g$) were together dispersed in 300 mL of toluene, and 4 g of γ-methacryloxypropyltrimethoxysilane was added to the dispersion, and the mixture was thermally refluxed for 2 hours. Toluene was distilled off under a reduced pressure with an evaporator, and the powder obtained was crushed, to give a hybrid surface treatment powder, in which the barium glass powder and the Aerosil powder were homogeneously mixed. This was referred to as an inorganic powder A-5.

Production Example 6 of Inorganic Short Fiber

Production of Inorganic Short Fiber A-6

Two-hundred grams of a commercially available milled fiber (manufactured by Central Glass Fiber Co., Ltd., EFH30-31, average fiber length: 30 μm, average fiber diameter: 11 μm) was dispersed in 500 mL of ethanol, and 1 g of γ-methacryloxypropyltrimethoxysilane and 5 g of water were added to the dispersion, and the mixture was stirred at room temperature for 2 hours. The solvent was distilled off under a reduced pressure, and the residue was further dried at 90° C. for 3 hours, thereby surface-treating the milled fiber, to give an inorganic short fiber A-6.

Production Example 7 of Inorganic Particles

Production of Inorganic Powder A-7

One-hundred grams of a commercially available ultrafine particle alumina (manufactured by Nippon Aerosil Co., Ltd., AEROXIDE (registered trademark) Alu C, average primary particle size: 0.02 μm, BET specific surface area: 100 m$^2$/g) was surface-treated in the same manner as in Production Example 1 of Inorganic Particles with 15 g of γ-methacryloxypropyltrimethoxysilane and 500 g of water, to give an inorganic powder A-7.

Production Example 8 of Inorganic Particles

Production of Inorganic Powder A-8

In accordance with a method described in WO 2009/133913, an amorphous powder (refractive index: 1.549, average particle size: 6.3 μm, particle size range: 0.2 to 20 μm) containing fine silica-based particles and oxides containing a zirconium atom, a silicon atom, and an oxygen atom, coating the surface of the fine silica-based particles was obtained. One-hundred parts by weight of the resulting amorphous powder was surface-treated in the same manner as in Production Example 1 of Inorganic Particles with 25 parts by weight of γ-methacryloxypropyltrimethoxysilane and 500 g of water, to give an amorphous powder A-8.

Example 1-1

The amount 5.5 g of the surface-treated inorganic powder A-1 obtained in the above-mentioned Production Example was spread over a lower punch rod of a mold for press having a rectangular hole of 35 mm×25 mm. The powder was evenly spread by tapping, and an upper punch rod was set above the evenly spread powder, and subjected to uniaxial press (press pressure: 60 kN (68.6 MPa), time being 3 minutes) with a table press machine. The upper punch rod and the lower punch rod were taken off from the mold, and a press molded article in which the powder was aggregated was taken out. The size of the molded article was in a plate-like shape of 35×25×5 mm. The press molded article was immersed in a polymerizable monomer composition a. The immersed press molded article was allowed to stand at room temperature in a dark room for 12 hours, and thereafter, while keeping the state of immersion, the pressure was reduced, and the degassing was carried out (10 hPa, 10 minutes). The reduced pressure was released, and a molded article in which the polymerizable monomer was immersed was taken out, to give a semitransparent polymerizable monomer-immersed molded article. When this semitransparent polymerizable monomer-immersed molded article was visually confirmed, the presence of bubbles in the internal was not found. Next, the molded article in which a polymerizable monomer was immersed was placed on a slide glass, and the molded article was subjected to photoirradiation with a dental photoirradiation instrument (manufactured by Morita Tokyo MFG. Corp., αLight 2) for 5 minutes to carry out photopolymerization. The resulting cured product was heat-treated at 130° C. for 20 minutes with a hot air dryer, to give an intended mill blank.

Example 1-2

The same procedures as in Example 1-1 were carried out to produce mill blanks, except that in the method of Example 1-1, the molded article after uniaxial press was placed in a plastic bag, and subjected to a CIP treatment (170 MPa, time being 1 minute), to give a press molded article in which the inorganic powder A-1 was aggregated.

Examples 2 to 5 and 8 to 10

The same procedures as in Example 1-1 were carried out using an inorganic powder A-2 to -5, -7, and -8 and an inorganic short fiber A-6, to give similar plate-like shaped mill blanks without bubbles or defects as Examples 2 to 5, and 8 to 10.

Examples 6 and 7

Two-hundred grams of an inorganic powder listed in Table 1 was spread over a lower punch rod of a mold for press having a circular hole of 120 mmφ, the powder was evenly spread by tapping, an upper punch rod was set to the evenly spread powder, and the inorganic powder was subjected to uniaxial press (press pressure: 300 kN (26.5 MPa, the time being 5 minutes) with a press machine. The upper punch rod and the lower punch rod were taken off from the mold, and a molded article in which the powder was aggregated was taken out. The size of the molded article was in a disc shape of 120 mmφ×20 mm. The molded article was placed in a plastic bag, and subjected to a CIP treatment (350 MPa, 20 minutes), to give a press molded article in which the inorganic powder was aggregated. The press molded article was immersed in a polymerizable monomer composition b. The immersed press molded article was allowed to stand at room temperature in a dark room for 5 days, and thereafter, while keeping the state of immersion, the pressure was reduced, and the degassing was carried out (10 hPa, 30 minutes). The reduced pressure was released, and a molded article in which the polymerizable monomer was immersed was taken out, to give a semitransparent polymerizable monomer-immersed molded article. When this semitransparent polymerizable monomer-immersed molded article was visually confirmed, the presence of bubbles in the internal was not found. Next, the molded article in which a polymerizable monomer was immersed was placed on a slide glass, and the molded article was subjected to photoirradiation with a UV photogenerating instrument (manufactured by TOSHIBA CORPORATION, Black Light Fluorescent Lamp) for 60 minutes to carry out photopolymerization. The resulting cured product was heat-treated at 70° C. for 24 hours and further at 110° C. for 5 hours, with a hot air dryer, to give an intended mill blank.

Here, as to the mill blanks of Examples 1 to 11, the summary of the compositions is shown in Table 1.

TABLE 1

|  |  | Examples |  |  |  |  |  |
|---|---|---|---|---|---|---|---|
|  |  | 1-1 | 1-2 | 2 | 3 | 4 | 5 |
| Polymerizable Monomer-Containing Composition (Parts by Weight) | BisGMA | 50 | 50 | 50 | 50 | 50 | 50 |
|  | HD | 50 | 50 | 50 | 50 | 50 | 50 |
|  | UDMA | — | — | — | — | — | — |
|  | TEGDMA | — | — | — | — | — | — |
|  | U-4TH | — | — | — | — | — | — |
|  | D6E | — | — | — | — | — | — |
|  | NPG | — | — | — | — | — | — |
|  | HFPD | — | — | — | — | — | — |
|  | TMDPO | 0.5 | 0.5 | 0.5 | 0.5 | 0.5 | 0.5 |
|  | BPO | 1.0 | 1.0 | 1.0 | 1.0 | 1.0 | 1.0 |
|  | AIBN | — | — | — | — | — | — |
| Inorganic Filler |  | A-1 | A-1 | A-2 | A-3 | A-4 | A-5 |
| Press Molding |  | Uniaxial Press | Uniaxial Press + CIP Treatment | Uniaxial Press | Uniaxial Press | Uniaxial Press | Uniaxial Press |

|  |  | Examples |  |  |  |  |  |
|---|---|---|---|---|---|---|---|
|  |  | 6 | 7 | 8 | 9 | 10 | 11 |
| Polymerizable Monomer-Containing Composition (Parts by Weight) | BisGMA | — | — | 50 | 50 | 50 | — |
|  | HD | — | — | 50 | 50 | 50 | — |
|  | UDMA | 70 | 70 | — | — | — | — |
|  | TEGDMA | 30 | 30 | — | — | — | — |
|  | U-4TH | — | — | — | — | — | 30 |
|  | D6E | — | — | — | — | — | 30 |
|  | NPG | — | — | — | — | — | 25 |
|  | HFPD | — | — | — | — | — | 15 |
|  | TMDPO | — | — | 0.5 | 0.5 | 0.5 | — |
|  | BPO | 1.5 | 1.5 | 1.0 | 1.0 | 1.0 | — |
|  | AIBN | — | — | — | — | — | 1.5 |
| Inorganic Filler |  | A-3 | A-5 | A-6 | A-7 | A-8 | A-3 |
| Press Molding |  | Uniaxial Press + CIP Treatment | Uniaxial Press + CIP Treatment | Uniaxial Press | Uniaxial Press | Uniaxial Press | Uniaxial Press + CIP Treatment |

Comparative Example 1-1

Ten parts by weight of a polymerizable monomer-containing composition a used in Example 1-1 was taken into a glass mortar, and further an inorganic powder A-1 used in Example 1-1 was added thereto, and the mixture was homogeneously kneaded, thereby preparing a viscous, paste-like composition (so-called composite resin). At a point where the inorganic powder A-1 was added in an amount of 27 parts by weight, it was difficult to further carry out homogenous kneading. The composition was defoamed under vacuum, to give a polymerizable composition usable as a dental composite resin. The composition was filled into a mold, sandwiched between slide glass, and subjected to photopolymerization with a dental photoirradiation instrument (manufactured by Morita Tokyo MFG. Corp., αLight 2, irradiation for 5 minutes), to give a plate-like shaped cured product of 30×40×3 mm. The resulting cured product was heat-treated at 130° C. for 20 minutes with a hot air dryer.

Comparative Example 1-2

In Example 1-1, a mill blank was produced without press. Specifically, 5.5 g of an inorganic powder A-1 was taken in a rectangular transparent polypropylene container of 35 mm×25 mm, and a depth of 20 mm, and the powder was evenly spread by tapping. A polymerizable monomer-containing composition a was gently poured thereto from above the container, pouring until the container was filled up, and then allowed to stand in a dark room. After 24 hours, the monomer became compatible with the inorganic powder, and the monomer reached to the bottom of the container. While keeping in this state, the pressure was reduced, and the degassing was carried out (10 hPa, 10 minutes). The reduced pressure was released, and the supernatant polymerizable monomer in which the inorganic powder did not exist was removed by decantation. With visual examination, the monomer penetrated into the internal of the interparticles in all the powders, and the existence of the bubbles was not found in the internal thereof. While keeping in this state, the monomer was subjected to photoirradiation with a dental photoirradiation instrument (manufactured by Morita Tokyo MFG. Corp., αLight 2) for 5 minutes, to carry out photopolymerization. The resulting cured product (size being a plate-like shape of 35 mm×25 mm×12 mm) was taken out of a polypropylene container, and heat-treated at 130° C. for 20 minutes with a hot air dryer, to give a mill blank.

Comparative Example 2

Production Example of Porous Support

A commercially available aluminosilicate glass powder (manufactured by KURARAY NORITAKE DENTAL INC., Noritake Super Porcelain EX3) was classified, to give a powder having a particle size range of from 1 to 10 μm and an average particle size of 5 μm. The inorganic powder was subjected to a method up to uniaxial press in the same manner as in the method of Example 1-1, to give a pre-molded article. The pre-molded article was sintered at a temperature of from 930° to 980° C. for 2 hours, to give a porous support. The degree of close-packing of the porous support was 70%. The porous support was immersed in a mixed solvent of 1 g of γ-methacryloxypropyltrimethoxysilane, 5 g of water, 0.2 g of acetic acid, and 93.8 g of methoxypropanol. While keeping the state of immersion, the pressure was reduced, and the degassing was carried out (10 hPa, 10 minutes). The porous support was allowed to stand at room temperature for 24 hours while keeping the state of immersion. Thereafter, the porous support was taken out of the solution, and subjected to drying under a reduced pressure, and the solvent was distilled off from the support. The residue was further dried at 100° C. for 4 hours, the solvent was then distilled off under a reduced pressure, and the residue was further dried at 150° C. for 4 hours, thereby surface-treating the porous support. The porous support was immersed in a polymerizable monomer composition a. The immersed porous support was allowed to stand at room temperature in a dark room for 12 hours, and thereafter, while keeping the state of immersion, the pressure was reduced, and the degassing was carried out (10 hPa, 10 minutes). The reduced pressure was released, and a porous support in which the polymerizable monomer was immersed was taken out, to give a semitransparent polymerizable monomer-immersed support. When this semitransparent polymerizable monomer-immersed support was visually confirmed, the presence of a large number of bubbles was found in the internal. Next, the support in which a polymerizable monomer was immersed was placed on a slide glass, and subjected to photoirradiation with a dental photoirradiation instrument (manufactured by Morita Tokyo MFG. Corp., αLight 2) for 5 minutes, to carry out photopolymerization. The resulting cured product was heat-treated at 130° C. for 20 minutes with a hot air dryer, to give a mill blank.

Example 11

Using a mold having a hole of 35 mm×25 mm, 10 g of an inorganic powder A-3 was placed in the mold, and subjected to uniaxial press at 60 IN (68.6 MPa), to give a molded article of the inorganic powder. The molded article was vacuum-packed, and further subjected to a CIP treatment at 350 MPa for 20 minutes. The molded article was taken out of the vacuum package and placed in a beaker, and allowed to contact with a polymerizable monomer-containing composition c to penetrate the polymerizable monomer in the internal of the molded article. After 4 days passed, it was confirmed that all the monomers penetrated in the internal of the molded article, and a monomer-immersed molded article was vacuum-packed together with the separately prepared polymerizable monomer-containing composition c. In the vacuum-packed state, the vacuum package was subjected to thermal polymerization under applied pressure. Specifically, a vacuum package was placed in a treatment chamber (at room temperature) of a CIP apparatus (Dr. CHEF), manufactured by Kobe Steel Co., Ltd., and a pressure of 900 MPa was applied thereto. In this state, the treatment chamber was heated, and heated to 110° C. over 4 hours. After the state at 110° C. was maintained for 30 minutes, the pressure was recovered to an ambient pressure, and the vacuum package was taken out. As a result, the polymerizable monomer was allowed to polymerize and cure, to give a desired mill blank being homogenous and free of cracks. Here, the inorganic content of the mill blank was 74.0% by weight.

Test Example 1

The flexural strength of the resulting mill blank was measured in accordance with the following method. Specifically, a specimen (2 mm×2 mm×25 mm) was prepared from the mill blank produced with a diamond cutter. The specimen was immersed in water at 37° C. for 24 hours, and its flexural strength and flexural modulus were measured in accordance with a 3-point flexural test method with a span of 20 mm, using a universal testing machine (manufactured by Instron) with a crosshead speed set at 1 mm/min. The results are shown in Table 2. The larger the flexural strength and the flexural modulus, the more favorable, and the flexural strength is more preferably 120 MPa or more, and the flexural modulus is more preferably 8 GPa or more.

Test Example 2

The compression strength of the resulting mill blank was measured in accordance with the following method. Specifically, a specimen (3 mm×3 mm×3 mm) was prepared from the mill blank produced with a diamond cutter. The specimen was immersed in water at 37° C. for 24 hours, and its compression strength was measured using a universal testing machine (manufactured by Instron) with a crosshead speed set at 2 mm/min. The results are shown in Table 2. The larger the compression strength, the more favorable, and the compression strength is more preferably 400 MPa or more.

TABLE 2

|  | Inorganic Filler | Flexural Strength (MPa) | Flexural Modulus (GPa) | Compression Strength (MPa) |
| --- | --- | --- | --- | --- |
| Example 1-1 | A-1 | 171 | 12.8 | 540 |
| Example 1-2 | A-1 | 201 | 14.0 | 576 |
| Comparative Example 1-1 | A-1 | 115 | 7.9 | 373 |
| Comparative Example 1-2 | A-1 | 96 | 5.9 | 310 |
| Comparative Example 2 | Ceramics | 125 | 31.7 | 258 |
| Example 2 | A-2 | 168 | 11.7 | 605 |
| Example 3 | A-3 | 175 | 9.5 | 675 |
| Example 4 | A-4 | 162 | 11.3 | 552 |
| Example 5 | A-5 | 251 | 28.0 | 685 |
| Example 6 | A-3 | 198 | 11.6 | 705 |
| Example 7 | A-5 | 266 | 29.5 | 732 |
| Example 8 | A-6 | 175 | 21.2 | 405 |
| Example 9 | A-7 | 184 | 9.2 | 645 |
| Example 10 | A-8 | 182 | 10.1 | 521 |
| Example 11 | A-3 | 265 | 11.9 | 670 |

From the results of Example 1-1 and Comparative Example 1-1, it could be seen that in the mill blanks obtained from the same inorganic filler powder and the same polymerizable monomer, the flexural strength and the flexural modulus of the mill blank obtained according to the method of the present invention were greatly superior to those of a cured product obtained by a conventional method, specifically obtained by polymerization curing of a paste-like composite resin.

In addition, Comparative Example 1-2 is a mill blank produced without carrying out a press treatment for the inorganic filler powder, and it can be seen that the flexural strength and the flexural modulus are markedly low, so that the press treatment brings about great effects.

In addition, Example 1-2 and Example 1-1 are the comparison of the presence or absence of the CIP treatment, and the improvement in strength is found in Example 1-2 where the CIP treatment was carried out.

From the comparisons of Example 1-1 to 5, it can be seen that Example 5 where hybrid inorganic particles are used as an inorganic filler have remarkably excellent flexural strength and flexural modulus.

Test Example 3

The inorganic filler contents of the mill blanks obtained in Examples 1-1, 1-2, and 2 to 5 and Comparative Examples 1-1 and 1-2 were measured. The test was carried out as follows. About 0.5 g of a cured product was placed in a porcelain crucible, and calcinated in an electric furnace at 575° C. for 2 hours to burn off organic components. An ignition residue was measured from a weight difference of the porcelain crucible before and after the test, and the inorganic filler content per unit weight of the mill blank was calculated. The results are shown in Table 3. The inorganic filler content measured according to this method does not include a surface-treating agent previously treated with the inorganic powder, and the surface-treating agent is measured as an organic component.

TABLE 3

|   | Inorganic Filler Content (% by weight) |
|---|---|
| Example 1-1 | 81.8 |
| Example 1-2 | 84.1 |
| Comparative Example 1-1 | 68.9 |
| Comparative Example 1-2 | 60.2 |
| Example 2 | 80.2 |
| Example 3 | 70.1 |
| Example 4 | 70.5 |
| Example 5 | 90.2 |

As is clear from Table 3, the inorganic filler contents of the mill blanks obtained in Examples of the present invention are very high. Also, it could be seen from the comparison of Examples 1-1 and 1-2 that the inorganic powder contents can be further increased by a CIP treatment.

Examples 3-2 to 3-7

The same procedures as in the method of Example 3 were carried out using the same inorganic filler and the same polymerizable monomer-containing composition except that uniaxial press pressure was changed to a pressure listed in Table 4, to give similar plate-like shape mill blanks without bubbles and defects as Examples 3-2 to 3-7. With respect to the cured products obtained, the flexural strength and the flexural modulus were measured in the same manner as in Test Example 1, and the inorganic filler contents were measured in the same manner as in Test Example 3. The results are shown in Table 4. Here, the results for Example 3 are also shown together for the sake of comparison.

TABLE 4

| Example | Uniaxial Press Pressure | Flexural Strength (MPa) | Flexural Modulus (GPa) | Inorganic Filler Content (% by weight) |
|---|---|---|---|---|
| 3 | 60 kN (68.6 MPa) | 175 | 9.5 | 70.1 |
| 3-2 | 2 kN (2.3 MPa) | 152 | 7.5 | 64.2 |
| 3-3 | 6 kN (6.7 MPa) | 160 | 8.0 | 67.0 |
| 3-4 | 10 kN (11.4 MPa) | 167 | 8.5 | 68.2 |
| 3-5 | 30 kN (34.3 MPa) | 171 | 9.1 | 69.3 |
| 3-6 | 100 kN (114.3 MPa) | 185 | 10.7 | 73.0 |
| 3-7 | 150 kN (171.4 MPa) | 198 | 11.9 | 75.1 |

It was observed that according to an increase in the uniaxial press pressure, the flexural strength, the flexural modulus, and the inorganic filler content became higher, thereby improving mechanical strength.

Test Example 4

Initial abrasion property of the resulting mill blanks was measured in accordance with the following method. Specifically, a specimen (10 mm×10 mm×2 mm) was produced from the mill blanks produced with a diamond cutter. A clean smooth surface was polished with #600 abrasive paper under drying conditions, and thereafter the polished surface was polished with a polishing instrument under the conditions listed in the following Table 5. The gloss of this surface was expressed in a proportion assuming that mirror is 100% (gloss), with a glossmeter (manufactured by JEOL Ltd., VG-2000). An angle of the measurement was set at 60 degrees. The gloss of 65% or more is considered to be preferred, and that of 70% or more is considered to be more preferable.

TABLE 5

|   | Gloss (60°) Sample | |
|---|---|---|
|   | Silicon Point Brown (SHOFU, INC.) | Silicon Point Blue (SHOFU, INC.) |
| Polishing Conditions | #600 (dry)→Wet, low-speed (about 5,000 rpm) Silicon Point Brown 10 s → Silicon Point Blue 10 s | |
| Polishing Instrument | Engine for Dental Technique: Volvere RX (NSK) | |

Test Example 5

The gloss retention of the resulting mill blanks was measured in accordance with the following method. Specifically, a specimen (10 mm×10 mm×2 mm) was produced from the mill blanks produced with a diamond cutter. A clean smooth surface was polished with #1500 abrasive paper, #2000 abrasive paper, and #3000 abrasive paper, in that order, under drying conditions, and finally polished with a diamond paste with the same instrument as in Test Example 4 until the gloss reached 90%. The gloss of a specimen after subjecting the specimen produced herein to a toothbrush abrasion test {toothbrush: Between, Lion (hardness: regular), toothpaste: Dentor Clear MAX (manufactured by Lion Corporation), load: 250 g, test solution: distilled water/toothpaste=90/10 (v/v, 50 mL), the number of abrasion: 40,000 times} was measured. The results are shown in Table 6. If the residual gloss is 60% or more, gloss retention is considered to be favorable, and if the residual gloss is 65% or more, gloss retention is considered to be more favorable.

Test Example 6

Each of the mill blanks obtained in Examples 1-1 to -2, 2 to 7, 9, and 10 and Comparative Examples 1-1 to -2, and 2 was milled and polished to a semispherical sample having a diameter of 10 mm and a height of 10 mm, and the sample was then subjected to a test for abrasion resistance. In the test method, bovine front teeth were used as opposing teeth, and a labial side thereof is limited only to enamel parts. An object obtained by milling a flat surface in an elliptic shape having a major diameter of 15 mm or so was vibrated in a horizontal direction at an oscillation of 4 mm, and 100,000 cycles of steps were repeated, wherein one cycle comprised bringing the semispherical sample prepared from the mill blank mentioned above into contact with an impact to the bovine teeth at its edge side under a load of 15.6 kg/cm$^2$, and releasing the sample from the teeth again after 1 second. The specific gravity and weight of the mill blanks to be subjected to the test were measured before the test. After the test, the weight of the mill blanks dried at 70° C. for 1 day was measured, and the abrasion amount of blank was calculated from specific gravity and weight loss. The abrasion amount of the bovine teeth together subjected to the test was measured by wiping off water from the bovine teeth after the test, and measuring the abrasion amount thereof with a surface roughness meter (LASER FOCUS DISPLACEMENT MATER LT-8100, manufactured by KEYENCE). The results for the abrasion amount of the blank and the abrasion amount of the opposing teeth are shown in Table 6. The smaller the abrasion amount of the blank and the smaller the abrasion amount of the opposing teeth, the more favorable, and the abrasion amount of blank was more preferably 1.5 mm$^3$ or less, and the abrasion amount of opposing teeth was more preferably 0.01 mm$^3$ or less.

TABLE 6

| | Initial Abrasion Property, % | Gloss Retention, % | Abrasion Amount of Blank, mm$^3$ | Abrasion Amount of Opposing Teeth, mm$^3$ |
| --- | --- | --- | --- | --- |
| Example 1-1 | 80 | 72 | 1.397 | 0.0076 |
| Example 1-2 | 82 | 75 | 1.402 | 0.0070 |
| Comparative Example 1-1 | 76 | 67 | 1.842 | 0.0092 |
| Comparative Example 1-2 | 74 | 65 | 1.891 | 0.0090 |
| Comparative Example 2 | 48 | 50 | 1.382 | 0.0240 |
| Example 2 | 81 | 71 | 1.302 | 0.0065 |
| Example 3 | 90 | 88 | 1.240 | 0.0010 |
| Example 4 | 88 | 83 | 1.201 | 0.0020 |
| Example 5 | 72 | 71 | 0.952 | 0.0072 |
| Example 6 | 91 | 84 | 1.250 | 0.0028 |
| Example 7 | 71 | 70 | 0.901 | 0.0070 |
| Example 9 | 90 | 82 | 1.264 | 0.0018 |
| Example 10 | 85 | 80 | 1.282 | 0.0035 |

When the initial abrasion property exceeds 80%, it is said to have excellent abrasion property, and further when the gloss retention is 70% or more, it is considered to be favorable. When comparisons are made in Examples 1-1 and 1-2 where the mill blanks have high filler contents with Comparative Examples 1-1 and 1-2 where the mill blanks have low filler contents even while the same filler is used, the mill blanks of Examples 1-1 and 1-2 are found to be clearly superior in abrasion property and gloss retention. In addition, other examples also have excellent abrasion property and gloss retention. Comparative Example 2 is a mill blank obtained by immersing a monomer composition in a glass porous support, and allowing to cure, but the mill blank obtained has low abrasion property and low gloss retention. The smaller the abrasion amount of blank and the abrasion amount of opposing teeth, the more favorable. Similarly, when comparisons are made in Examples 1-1 and 1-2 where the mill blanks have high filler contents with Comparative Examples 1-1 and 1-2 where the mill blanks have low filler contents even while the same filler is used, the mill blanks of Examples 1-1 and 1-2 clearly have smaller abrasion amounts of blank and smaller abrasion amounts of opposing teeth. In addition, other examples also have small abrasion amounts of blank and small abrasion amounts of opposing teeth. Comparative Example 2 is a mill blank obtained by immersing a monomer composition in a glass porous support, and allowing to cure, but the mill blank has a markedly large abrasion amount of opposing teeth.

Comparative Example 1-3

A polymerizable monomer-containing composition a used in Example 1-1 was placed in a glass mortar in an amount of 18.2 parts by weight, and further an inorganic powder A-1 in an amount of 81.8 parts by weight, the same amount as the content of the inorganic powder A-1 in Example 1-1, which was clarified in Test Example 2, and the mixture was tried to be homogeneously kneaded. However, the monomer and the inorganic powder could not be made homogeneously compatible to each other, so that a paste-like composition could not be obtained. This fact shows that a composition having a very high inorganic powder content, of the same level as in Example 1-1 could not be obtained by a method of kneading a polymerizable monomer and an inorganic powder.

Example 12

A fine alumina powder manufactured by Nippon Aerosil Co., Ltd. "AEROXIDE (registered trademark) Alu130" (average primary particle size: about 0.02 μm, BET specific surface area: 130 m$^2$/g) was subjected to surface treatment with 15% by weight of an organophosphoric acid compound (10-methacryloyloxydecyl dihydrogen phosphate: commonly known as MDP), to give a surface-treated fine alumina powder. The powder was filled in a rubber tube having an inner diameter of 20 mm and a length of 10 cm, and the rubber tube was tightly sealed, and further vacuum-packed with a plastic bag. In this state, the vacuum package was subjected to a CIP treatment (600 MPa for 20 minutes), to give a press molded article in a rounded bar shape. A polymerizable monomer composition c, the same one as in Example 11, was immersed in the molded article, and the monomer-immersed molded article was vacuum-packed. In this state, the vacuum package was immersed in a water bath at 70° C. for 12 hours, the package was taken out of the water bath, and further heated at 120° C. for 3 hours, and the monomer was allowed to polymerize and cure, to give a mill blank. As to the resulting cured product, the flexural strength and the flexural modulus were measured in the same manner as in Test Example 1, and the inorganic filler content was measured in the same manner as in Test Example 3. The results are shown in Table 7.

Example 13

The same procedures as in Example 12 were carried out in the CIP treatment, the immersion of the polymerizable monomer, and the polymerization curing, using a methacrylsilane-treated fine spherical silica powder manufactured by Admatechs Co., Ltd., "ADMANANO YA010C-SM1" (average primary particle size: 0.01 μm, BET specific surface area: 300 m²/g), to give a mill blank. As to the resulting cured product, the flexural strength and the flexural modulus were measured in the same manner as in Test Example 1, and the inorganic filler content was measured in the same manner as in Test Example 3. The results are shown in Table 7.

Example 14

The same procedures as in Example 12 were carried out in the CIP treatment, the immersion of the polymerizable monomer, and the polymerization curing, using a methacrylsilane-treated fine spherical silica powder manufactured by Admatechs Co., Ltd., "ADMANANO YC100C-SM1" (average particle size: 0.1 μm, particle size range: 0.08 to 0.12 μm), to give a mill blank. As to the resulting cured product, the flexural strength and the flexural modulus were measured in the same manner as in Test Example 1, and the inorganic filler content was measured in the same manner as in Test Example 3. The results are shown in Table 7.

Example 15

Glass fiber manufactured by Nittobo (Nitto Boseki Co., Ltd.) (filament diameter: 11 μm) was pulverized with a ball-mill, and classified, to give a short fiber-form E glass powder having a fiber length range of from 130 to 20 μm. The powder was surface-treated with 0.5% by weight of γ-methacryloxypropyltrimethoxysilane, to give a surface-treated glass powder. The same procedures as in Example 12 were carried out in the CIP treatment, the immersion of the polymerizable monomer, and the polymerization curing, to give a mill blank. As to the resulting cured product, the flexural strength and the flexural modulus were measured in the same manner as in Test Example 1, and the inorganic filler content was measured in the same manner as in Test Example 3. The results are shown in Table 7.

Example 16

A hydroxyapatite powder manufactured by Taihei Chemical Industrial Co., Ltd. was pulverized with a ball-mill, and classified, to give a powder having an average particle size of 1.5 μm, a particle size range of from 0.1 to 5 μm, and a specific surface area of 50 m²/g. The powder was surface-treated with 5% by weight of an organophosphoric acid compound (10-methacryloyloxydecyl dihydrogen phosphate: commonly known as MDP), to give a surface-treated fine hydroxyapatite powder. The same procedures as in Example 12 were carried out in the CIP treatment, the immersion of the polymerizable monomer, and the polymerization curing, to give a mill blank. As to the resulting cured product, the flexural strength and the flexural modulus were measured in the same manner as in Test Example 1, and the inorganic filler content was measured in the same manner as in Test Example 3. The results are shown in Table 7.

TABLE 7

|  | Flexural Strength (MPa) | Flexural Modulus (GPa) | Inorganic Filler Content (% by weight) |
| --- | --- | --- | --- |
| Example 12 | 210 | 13.5 | 80.5 |
| Example 13 | 165 | 10.3 | 75.1 |
| Example 14 | 170 | 14.6 | 81.5 |
| Example 15 | 205 | 27.5 | 82.5 |
| Example 16 | 121 | 18.9 | 90.1 |

In Examples 12 to 16, as methods of pressing powders using various kinds of powders, the powders were subjected to high-pressure press using CIP alone, without using uni-axial press. In all the Examples, excellent press molded articles are obtained, and further the press molded article was allowed to contact with a polymerizable monomer-containing composition, so that the monomer composition penetrates in the internal of the molded article, and is further allowed to polymerize, thereby giving an excellent mill blank.

Example 17

Production of Mill Blank Having Multi-Layered Structure

Fifty parts by weight of 2,2,4-trimethylhexamethylenebis(2-carbamoyloxyethyl)]dimethacrylate (commonly known as UDMA), 25 parts by weight of triethylene glycol dimethacrylate (commonly known as TEGDEMA), and 25 parts by weight of tricyclodecanedimethanol dimethacrylate as polymerizable monomers, and 0.5 parts by weight of 2,2-azobisisobutyronitrile (commonly known as AIBN) as a thermal polymerization catalyst were homogeneously mixed to dissolve, to give a polymerizable monomer-containing composition d.

On the other hand, an inorganic powder A-1 was added with Japan Pharmacopeia titanium oxide, black iron oxide, red iron oxide (red oxide), and yellow iron oxide each in a slight amount as pigments, and the mixture was homogeneously mixed with a rotary ball-mill, to prepare a colored inorganic powder.

The amount 5.5 g of the colored inorganic powder was filled in a mold for press in the same manner as in Example 1-1, and subjected to press at a press pressure of 60 kN (68.6 MPa) for 1 minute. The upper punch rod was taken off, 2.5 g of an inorganic powder A-3 was filled from above the side to which the inorganic powder was pressed, and the powder was evenly spread by tapping. The upper punch rod was again placed thereon, and the powder was subjected to a press treatment in the same manner with a table press machine at 60 kN (68.6 MPa) for 3 minutes. The upper punch rod and the lower punch rod were removed from the mold, and a press molded article in which two kinds of powders are aggregated in a layered form was taken out. The size of the molded article was in a plate-like shape of 35×25×10 mm. This molded article was further subjected to a CIP treatment (170 MPa, time being 2 minutes), to give a press molded article in which two kinds of powders are aggregated in a layered form. The press molded article was immersed in a polymerizable monomer-containing composition d mentioned above. The immersed press molded article was allowed to stand at room temperature in a dark room for 12 hours, and thereafter, while keeping the state of immersion, the pressure was reduced, and the degassing was carried out (10 hPa, 10 minutes). The reduced pressure was released, and a molded article in which the polymerizable monomer was immersed was taken out. As a result, with visual examination, the monomer penetrated to all the internals of the powder molded article, and the presence of the bubbles was not recognized in the internal.

The molded article in which the monomer was immersed was placed in a plastic bag, and vacuum-packed in a state that the air would not mix therewith. The vacuum package was placed in a hot air dryer, and subjected to thermal polymerization at 85° C. for 2 hours, and then at 120° C. for 1 hour, to give a mill blank. The mill blank had a two-layer structure consisting of a dentine color layer having relatively high non-transmittance and a semitransparent colorless layer.

Further, the mill blank was fabricated into the maxillary first molar tooth crown using a commercially available CAD/CAM system (CEREC System of Sirona Dental Systems, Inc.). As a result, crown having excellent aesthetic properties was fabricated.

Example 18

An inorganic powder A-3 was added with Japan Pharmacopeia titanium oxide, black iron oxide, red iron oxide (red oxide), and yellow iron oxide each in a slight amount as pigments, and the mixture was homogeneously mixed with a rotary ball-mill, to prepare a deep color inorganic powder A-3-1 and a pale color inorganic powder A-3-2. In addition, an intermediate color inorganic powder A-3-3 obtained by homogeneously mixing A-3-1 and A-3-2 at a ratio of 1:1 was also prepared.

Six grams of the pale color inorganic powder A-3-2 was filled in a mold for press in the same manner as in Example 1-1, and subjected to press at a press pressure of 10 kN (11.4 MPa) for 1 minute. The upper punch rod was taken off, 4 g of the intermediate color inorganic powder A-3-3 was filled from above the side to which the inorganic powder was pressed, and the powder was evenly spread by tapping. The upper punch rod was again placed thereon, and the powder was subjected to a press treatment in the same manner with a table press machine at 20 kN (22.9 MPa) for 3 minutes. The upper punch rod was taken off, and 4 g of the deep color inorganic powder A-3-1 was filled from above the side to which the inorganic powder was pressed, and the powder was evenly spread by tapping. The upper punch rod was again placed thereon, and the powder was subjected to a press treatment in the same manner with a table press machine at 60 kN (68.6 MPa) for 3 minutes. The upper punch rod and the lower punch rod were removed from the mold, and a press molded article in which three color powders were aggregated in a layered form was taken out. The size of the molded article was a plate-like shape of 35×25×15 mm. The press molded article was immersed in a polymerizable monomer-containing composition b mentioned above. The immersed press molded article was allowed to stand at room temperature in a dark room for 12 hours, and thereafter, while keeping the state of immersion, the pressure was reduced, and the degassing was carried out (10 hPa, 10 minutes). The reduced pressure was released, and a molded article in which the polymerizable monomer was immersed was taken out. With visual examination, the monomer penetrated to all the internals of the powder molded article, and the presence of the bubbles was not recognized in the internal. Next, the molded article in which the polymerizable monomer was immersed was placed on a slide glass, and subjected to photoirradiation with a UV photogenerator (manufactured by TOSHIBA CORPORATION, Black Light Fluorescent Lamp) for 60 minutes to carry out photopolymerization. The resulting cured product was heat-treated at 70° C. for 24 hours, and further heat-treated at 110° C. for 5 hours with a hot air dryer, to give an intended mill blank.

Further, the mill blank was produced into a mill blank piece of 14.5 mm ×18 mm ×14.5 mm with a diamond cutter, and fabricated into the maxillary first molar tooth crown with a commercially available CAD/CAM system (CEREC System of Sirona Dental Systems, Inc.). As a result, a crown having excellent aesthetic properties having a color tone similar to natural teeth for which gloss was found without polishing treatment was fabricated.

In addition, a plate-like shape specimen (10 mm ×10 mm ×1 mm) was cut out from the mill blank with a diamond cutter which was used in parallel to each of hues of the mill blanks produced, and thereafter the smooth surface was polished with #1500 abrasive paper, #2000 abrasive paper, and #3000 abrasive paper, in that order, under drying conditions. The color degree of each hue was measured with a spectrocolorimeter (CM-3610d, manufactured by Minolta, D65 light source). The measurement results are shown in Table 8.

TABLE 8

|  | L* | a* | b* | ΔL* |
|---|---|---|---|---|
| Pale Color Layer | 84.2 | 1.0 | 19.4 | 13.1 |
| Intermediate Color Layer | 79.0 | 3.8 | 24.8 | 11.2 |
| Deep Color Layer | 73.8 | 6.6 | 30.1 | 10.8 |

The color tone of the pale color layer was a color tone appropriate as enamel, and the color tone of the deep color layer was a color tone appropriate as neck of tooth. The color tone of the intermediate color layer therebetween was a color tone nearly midway color tone of the pale color layer and the deep color layer, and this color was a color tone appropriate as a dentine color. In other words, the crowns obtained from the mill blanks of the present invention reproduced the color tone structure resembling natural teeth. Further, because of the presence of the intermediate color layer, there was an advantageous merit that the boundary parts of the colors are seemingly not outstanding.

From the above results, by using the method of the present invention, it could be seen that a dental mill blank having a high inorganic powder content and excellent mechanical strength, and reproducing color changes similar to the natural teeth was obtained.

INDUSTRIAL APPLICABILITY

When the method of the present invention is used, a dental mill blank having a high inorganic powder content and excellent mechanical strength is obtained. In addition, the dental mill blank of the present invention is suitably used as a dental mill blank. In other words, by machining a mill blank using a CAD/CAM system, the mill blank is suitably used in the fabrication of a dental prosthesis having high mechanical strength and excellent gloss retention.

The invention claimed is:

1. A method for producing a dental mill blank, the method comprising:
   press molding an inorganic filler to obtain an inorganic filler molded article;
   immersing the inorganic filler molded article in a polymerizable monomer-comprising composition; and polymerizing and curing the polymerizable monomer-comprising composition, to obtain a dental mill blank,
wherein the polymerizable monomer-comprising composition further comprises at least one of a photopolymerization initiator and a thermal polymerization initiator.

2. The method according to claim 1, wherein the press molding is a uniaxial press molding.

3. The method according to claim 2, Therein a press pressure during the uniaxial press molding is 10 MPa or more.

4. The method according to claim 1, wherein the press molding comprises a cold isotactic press molding.

5. The method according to claim 4, wherein a press pressure during the cold isotactic press molding is 30 MPa or more.

6. The method according to claim 1, wherein the polymerizing and curing occurs in a vacuum state.

7. The method according to claim 1, wherein the polymerizing and curing is carried out under an applied pressure.

8. The method according to claim 7, wherein the applied pressure is 50 MPa or more.

9. The method according to claim 1, wherein the polymerizable monomer-comprising composition further comprises the photopolymerization initiator and the thermal polymerization initiator.

10. The method according to claim 9, wherein the polymerizing and curing comprises, subsequent to a photopolymerization, a thermal polymerization.

11. The method according to claim 1, wherein the inorganic filler comprises inorganic particles having an average particle size of from 0.001 to 10 µm, and a particle size range of from 0.0005 to 50 µm.

12. The method according to claim 1, wherein the inorganic filler comprises inorganic particles having an average particle size of from 0.1 to 1 µm, and a particle size range of from 0.05 to 5 µm.

13. The method according to claim 12, wherein the inorganic filler comprises spherical particles.

14. The method according to claim 1, wherein the inorganic filler comprises ultrafine inorganic panicles having an average particle size of from 0.001 to 0.1 µm , and a specific surface area of from 500 to 30 $m^2/g$.

15. The method according to claim 1, wherein the inorganic filler comprises inorganic particles that are aggregated particles produced by aggregating ultrafine inorganic particles having an average particle size of from 0.001 to 0.1µm, and a specific surface area of from 500 to 30 $m^2/g$, and the particle sizes of the aggregated particles range from 1 to 20µm.

16. The method according to claim 1, wherein the inorganic filler comprises
ultrafine inorganic particles having an average particle size of from 0.001 to 0.1 µm, and a specific surface area of from 500 to 30 $m^2/g$, and
inorganic particles having an average particle size of from 0.2 to 2 µm and a particle size range of from 0.1 to 10 µm.

17. The method according to claim 1, wherein the inorganic filler comprises inorganic particles previously subjected to a surface treatment.

18. A dental mill blank obtained by the method according to claim 1, wherein the inorganic filler does not include a calcium phosphate.

19. The dental mill blank according to claim 18,
wherein the inorganic filler molded article is a molded article produced by press molding two or more kinds of different inorganic particles into a layered form.

20. A dental prosthesis fabricated by a method comprising machining the dental mill blank according to claim 18.

21. A dental mill blank obtained by the method according to claim 1, wherein:
the mill blank comprises ultrafine inorganic particles having an average particle size of from 0.001 to 0.1 µm in an amount of from 65 to 95% by weight of the mill blank: and
the inorganic filler does not include a calcium phosphate.

22. A dental mill blank obtained by the method according to claim 1, wherein:
the dental mill blank comprises inorganic particles having an average particle size of from 0.1 to 1 µm in an amount of from 80 to 95% by weight of the mill blank: and
the inorganic filler does not include a calcium phosphate.

23. A dental mill blank obtained by the method according to claim 1, wherein:
the dental mill blank comprises ultrafine inorganic particles having an average particle size of from 0.001 to 0.1 µm and inorganic particles having an average particle size of from 0.2 to 2 µm in a total amount of from 80 to 96% by weight of the mill blank: and
the inorganic filler does not include a calcium phosphate.

24. The method of claim 1, wherein the dental mill blank does not contain internal bubbles.

* * * * *